United States Patent
Garcia et al.

(10) Patent No.: US 9,738,696 B2
(45) Date of Patent: Aug. 22, 2017

(54) SUPERKINES AND SYNTHEKINES: REPURPOSED CYTOKINES WITH NEW AND ENHANCED SIGNALING ACTIVITIES

(71) Applicant: The Board of Trustees of the Leland Stanford Junior University, Stanford, CA (US)

(72) Inventors: K. Christopher Garcia, Menlo Park, CA (US); Darren L. Bates, Oak Park, CA (US); Ignacio Moraga, Don Benito (ES)

(73) Assignee: THE BOARD OF TRUSTEES OF THE LELAND STANFORD JUNIOR UNIVERSITY, Palo Alto, CA (US)

( * ) Notice: Subject to any disclaimer, the term of this patent is extended or adjusted under 35 U.S.C. 154(b) by 0 days.

(21) Appl. No.: 14/419,873

(22) PCT Filed: Aug. 8, 2013

(86) PCT No.: PCT/US2013/054164
§ 371 (c)(1),
(2) Date: Feb. 5, 2015

(87) PCT Pub. No.: WO2014/074186
PCT Pub. Date: May 15, 2014

(65) Prior Publication Data
US 2016/0244499 A1    Aug. 25, 2016

Related U.S. Application Data

(60) Provisional application No. 61/681,490, filed on Aug. 9, 2012, provisional application No. 61/725,791, filed
(Continued)

(51) Int. Cl.
*A61K 38/00* (2006.01)
*C07K 14/54* (2006.01)
*C07K 14/52* (2006.01)

(52) U.S. Cl.
CPC .......... *C07K 14/5406* (2013.01); *C07K 14/52* (2013.01); *A61K 38/00* (2013.01)

(58) Field of Classification Search
CPC ... C07K 14/5406; C07K 14/52; A61K 39/395
See application file for complete search history.

(56) References Cited

U.S. PATENT DOCUMENTS 6,130,318 A * 10/2000 Wild .................. C07K 14/5406
424/85.1
6,335,426 B1 * 1/2002 Shanafelt ........... C07K 14/5406
424/85.2

FOREIGN PATENT DOCUMENTS

WO    WO 2011/106779 A1    9/2011

OTHER PUBLICATIONS

UniProtKB database P05112 (Aug. 13, 1987).*
(Continued)

*Primary Examiner* — Cherie M Stanfield
(74) *Attorney, Agent, or Firm* — Morgan Lewis & Bockius LLP

(57) ABSTRACT

Disclosed herein are IL-4 cytokine compositions with enhanced biological activity having increased selectivity for IL-4 cytokine receptors, and methods for their use. These compositions encompass interleukin-4 (IL-4) muteins. The disclosed methods encompass administering an IL-4 to treat neoplastic diseases, autoimmune diseases, infectious diseases or for expanding a hematopoietic cell population.

14 Claims, 23 Drawing Sheets

Related U.S. Application Data on Nov. 13, 2012, provisional application No. 61/825,980, filed on May 21, 2013.

(56) References Cited

OTHER PUBLICATIONS

Creusot, Remi J. and Ignacio Moraga, "Superkines, cytokines displaying better targeted functions," *Med. Sci (Paris)*, 29:4(345-349) (2013).

Kahlon et al., "Specific Recognition and Killing of Glioblastoma Multiforme by Interleukin 13-Zetakine Redirected Cytolytic T Cells," *Cancer Research*, 64:9160-9166 (2004).

Levin, et al., "Exploiting a natural conformational switch to engineer an interleukin-2 'superkine'," *Nature* 484:529-533 (A & B) (2012).

Creusot et al., "Engineering cell-type selective immune responses using mechanism-based designer IL-4 cytokines," *The Journal of Immunology*, 186:57.8 (2011).

Junttila et al., "Redirecting cell-type specific cytokine responses with engineered interleukin-4 superkines," *Nature Chemical Biology*, 8:12, pp. 990-998 (2012).

Schnare et al., "Specific Antagonism of Type I IL-4 Receptor with a Mutated Form of Murine IL-4," *The Journal of Immunology*, 161:7, pp. 3484-3492 (1998).

Bates, D. L, et al., "3QB7: Interleukin-4 mutant RGA bound to cytokine receptor common gamma," <<RCSB PDB>> *Protein Data Bank*, pp. 1-2 (Apr. 25, 2012).

\* cited by examiner

FIGURE 20
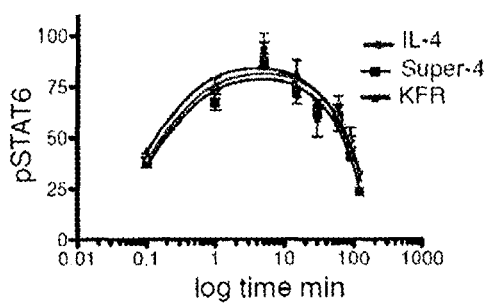
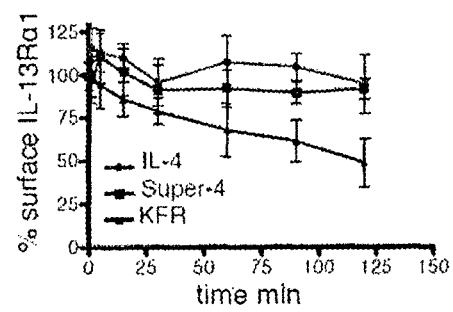
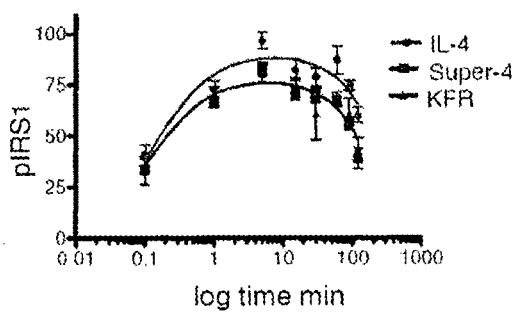
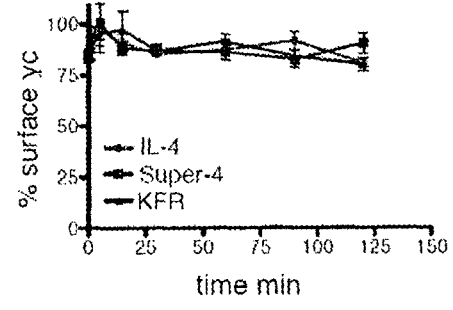

FIGURE 22
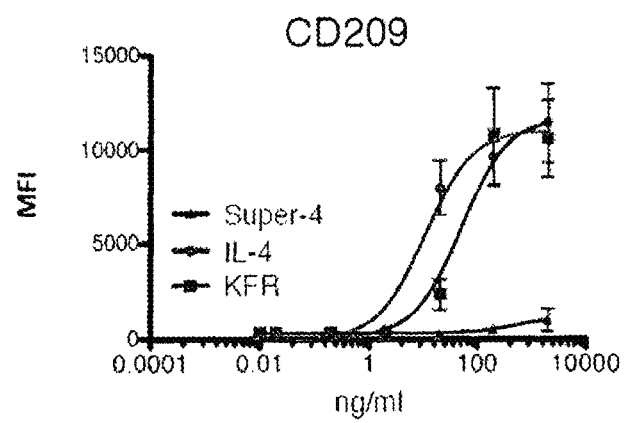
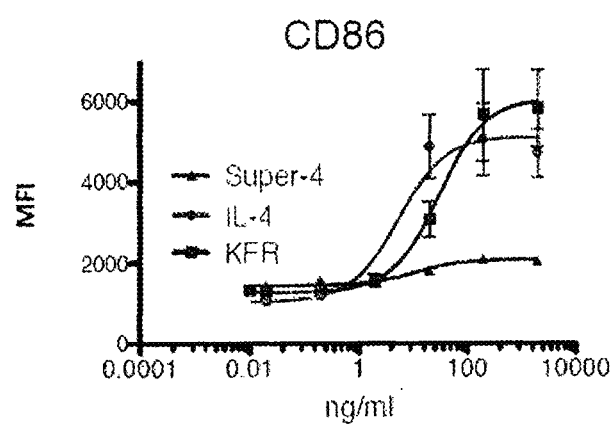

SEQUENCE LISTING

<160> NUMBER OF SEQ ID NOS: 4

<210> SEQ ID NO 1
<211> LENGTH: 153
<212> TYPE: PRT
<213> ORGANISM: Homo sapiens

<400> SEQUENCE: 1

```
Met Gly Leu Thr Ser Gln Leu Leu Pro Pro Leu Phe Phe Leu Leu Ala
1               5                   10                  15

Cys Ala Gly Asn Phe Val His Gly His Lys Cys Asp Ile Thr Leu Gln
            20                  25                  30

Glu Ile Ile Lys Thr Leu Asn Ser Leu Thr Glu Gln Lys Thr Leu Cys
        35                  40                  45

Thr Glu Leu Thr Val Thr Asp Ile Phe Ala Ala Ser Lys Asn Thr Thr
    50                  55                  60

Glu Lys Glu Thr Phe Cys Arg Ala Ala Thr Val Leu Arg Gln Phe Tyr
65                  70                  75                  80

Ser His His Glu Lys Asp Thr Arg Cys Leu Gly Ala Thr Ala Gln Gln
                85                  90                  95

Phe His Arg His Lys Gln Leu Ile Arg Phe Leu Lys Arg Leu Asp Arg
            100                 105                 110

Asn Leu Trp Gly Leu Ala Gly Leu Asn Ser Cys Pro Val Lys Glu Ala
        115                 120                 125

Asn Gln Ser Thr Leu Glu Asn Phe Leu Glu Arg Leu Lys Thr Ile Met
    130                 135                 140

Arg Glu Lys Tyr Ser Lys Cys Ser Ser
145                 150
```

<210> SEQ ID NO 2
<211> LENGTH: 78
<212> TYPE: DNA
<213> ORGANISM: Artificial Sequence
<220> FEATURE:
<223> OTHER INFORMATION: unassigned DNA

<400> SEQUENCE: 2

```
ctagtggtgg tggtggttct ggtggtggtg gttctggtgg tggtggttct gctagccaca    60
agtgcgatat caccttac                                                  78
```

<210> SEQ ID NO 3
<211> LENGTH: 56
<212> TYPE: DNA
<213> ORGANISM: Artificial Sequence
<220> FEATURE:
<223> OTHER INFORMATION: unassigned DNA

<400> SEQUENCE: 3

```
cagatctcga gcaagtcttc ttcggagata agcttttgtt cgccaccaga ggatcc        56
```

<210> SEQ ID NO 4
<211> LENGTH: 129
<212> TYPE: PRT
<213> ORGANISM: Artificial Sequence
<220> FEATURE:
<223> OTHER INFORMATION: homo sapiens

<400> SEQUENCE: 4

```
His Lys Cys Asp Ile Thr Leu Gln Glu Ile Ile Lys Thr Leu Asn Ser
1               5                   10                  15

Leu Thr Glu Gln Lys Thr Leu Cys Thr Glu Leu Thr Val Thr Asp Ile
            20                  25                  30

Phe Ala Ala Ser Lys Asn Thr Thr Glu Lys Glu Thr Phe Cys Arg Ala
        35                  40                  45

Ala Thr Val Leu Arg Gln Phe Tyr Ser His His Glu Lys Asp Thr Arg
    50                  55                  60
```

-continued

```
Cys Leu Gly Ala Thr Ala Gln Gln Phe His Arg His Lys Gln Leu Ile
65                  70                  75                  80

Arg Phe Leu Lys Arg Leu Asp Arg Asn Leu Trp Gly Leu Ala Gly Leu
                85                  90                  95

Asn Ser Cys Pro Val Lys Glu Ala Asn Gln Ser Thr Leu Glu Asn Phe
            100                 105                 110

Leu Glu Arg Leu Lys Thr Ile Met Arg Glu Lys Tyr Ser Lys Cys Ser
        115                 120                 125

Ser
```

SUPERKINES AND SYNTHEKINES: REPURPOSED CYTOKINES WITH NEW AND ENHANCED SIGNALING ACTIVITIES

CROSS-REFERENCE TO RELATED APPLICATIONS

This application is based on International Application No. PCT/US2013/054164, filed Aug. 8, 2013, and claims priority to U.S. Provisional Patent Application No. 61/825,980, filed May 21, 2013; U.S. Provisional Patent Application No. 61/725,791, filed Nov. 13, 2012; and U.S. Provisional Patent Application No. 61/681,490, filed Aug. 9, 2012, the disclosures of each of which are incorporated herein by reference in their entirety for all purposes.

BACKGROUND

Cytokines are small cell-signaling molecules that are secreted by numerous cells and are a category of signaling molecules used extensively in intercellular communication. Cytokines regulate key cellular functions, including differentiation, proliferation and apoptosis/anti-apoptosis.

Many cytokines mediate stimulation by first interacting with a relatively high affinity cytokine receptor chain, usually designated "a," followed by a relatively low affinity interaction with a receptor chain that is shared among different cytokines, a shared receptor chain. Binding of a cytokine to the first high affinity receptor creates a composite surface that the shared receptor chain can then bind.

Interleukin-4 (IL-4) typifies such cytokines. The primary binding chain of IL-4 is IL-4 Receptor α(IL-4Rα). The IL-4/IL-4Rα complex serves as a ligand for the second component of the IL-4 receptor, γc. Additionally, the IL-4/IL-4Rα complex serves as a ligand for the interleukin-13 (IL-13) Receptor α1 (IL-13Rα1). Unlike IL-4, IL-13 does not bind to IL-4Rα however, IL-13/IL-13Rα1 complex binds does bind to IL-4Rα.

Because IL-4 and IL-13 can signal through distinct receptors, it can be postulated that they are be able to activate different signal transduction pathways. Indeed, γc activates the tyrosine kinase Janus kinase 3 (JAK3), whereas IL-13Rα1 activates Tyk2 and JAK2. Activated JAKs mediate the phosphorylation of the cytoplasmic tail of IL-4R on conserved tyrosine residues that serve as docking sites for proteins containing Src homology 2 (SH2) domains. Three closely clustered tyrosine residues serve as docking sites for signal transducer and activator of transcription 6 (STAT6), a transcription factor selectively coupled to the IL-4Rα chain. The binding of IL-13 to IL-13Rα1 also activates STAT6 through the binding of IL-4Rα by IL-13/IL-13Rα1 complex.

In addition to STAT6, IL-4 recruits and activates IRS-2. Structure-function analyses have revealed that a tyrosine residue [Tyr$^{497}$, part of the insulin/IL-4R motif (I4R)] on the transmembrane domain of IL-4Rα is necessary for the docking of IRS-2 to IL-4Rα after IL-4Rα has been activated by IL-4. JAK1 and JAK3 then phosphorylate IL-4Rα-bound IRS-2. The activation of IRS-2 leads to the activation of phosphoinositide 3-kinase (PI3K) and the downstream protein serine/threonine kinase Akt, a pathway that is thought to mediate growth and survival signals in many cell types. Indeed, this pathway is important in IL-4-mediated growth in cells expressing the type I IL-4R (NK cells, T cells, and B cells).

Although IL-4Rα is ubiquitously present, $γ_c$, but not IL-13Rα1 is found on T cells, natural killer (NK) cells, basophils, mast cells, and most mouse B cells (most human B cells express both $γ_c$, and IL-13Rα1). Consequently, IL-4, but not IL-13, promotes the differentiation of naïve T cells into $T_H2$ cells, and IL-4 appears much more important than IL-13 for the induction of mouse IgE responses.

Some bone marrow-derived cells, including macrophages and dendritic cells, express both $γ_c$ and IL-13Rα1 and consequently respond to both IL-4 and IL-13. Differences in the relative abundance of these two receptor subunits on different subpopulations of these cells may account, in part, for their relative responsiveness to IL-4 versus IL-13. IL-13Rα1, but little or no $γ_c$ subunit, is found on most non-bone marrow-derived cells, including smooth muscle and epithelial cells; consequently, IL-4 has no inherent advantage over IL-13 in stimulating these cells.

In the early 1990's, clinical trials were performed utilizing IL-4 to treat cancer. It had been observed that IL-4 induces growth arrest and apoptosis in leukemia lymphoblasts in vitro. These observations were confirmed in experiments with human leukemic cells engrafted in immunodeficient mice. Unfortunately, the clinical usefulness of IL-4 is limited by the pleiotropic activities of the cytokine including renal, hepatic, neurologic, and gastrointestinal toxicities as well as vascular leak syndrome, which is associated with binding of IL-4 to non-hematopoietic cells. Thus, the use of "wild-type" IL-4 as a therapeutic is limited by its capacity to bind cell types that cause undesirable responses.

Consequently, a need in the art exists for molecules with increased selectively for one receptor relative to another; using IL-4 as an example, increased selectivity for γc relative to IL-13Rα1 can be advantageous or vice a versa.

Furthermore, some toxicity associated with the use of wild-type cytokines can be the result of the administration of high doses. Thus, molecules which can achieve activation of the desired shared receptor with lower doses would also be advantageous.

Accordingly, the instant invention addresses these and other needs in the art.

BRIEF DESCRIPTION OF THE DRAWINGS

FIG. 20 illustrates receptor downregulation and STAT6 and IRS1 phosphorylation kinetics induced by IL-4 and the two superkines in monocytes. Monocytes were stimulated with 50 nM of IL-4 or the two superkines for the indicated times and cells were either (a-b) fixed and permeabilized with 100% methanol for 30 min and stained with phospho-STAT6 and phospho-IRS1 antibodies; or (c-d) were stained with anti-IL-13Rα1 or γc specific antibodies and 30 min at 4° C., to prevent receptor internalization, fixed with 4% PFA and analyzed by flow cytometry. Data (mean and SEM) are from four healthy donors.

FIG. 22 illustrates dendritic cells differentiation potency exhibited by the IL-4 superkines. CD14+ monocytes were isolated (>97% purity) and subsequently cultured with 50 ng/mL GM-CSF alone or with the indicated concentrations of IL-4, KFR or super-4. Cells were processed on day 6-7 and stained with fluorescently labeled antibodies against CD86, CD209. Dendritic cell differentiation was assessed by flow cytometry with a BD LSRII flow cytometer and the mean fluorescent intensity (MFI) was determined on the FlowJo software (Treestar). Data represent mean±SEM from 3 healthy donors.

BRIEF SUMMARY OF THE INVENTION

Figure 1:
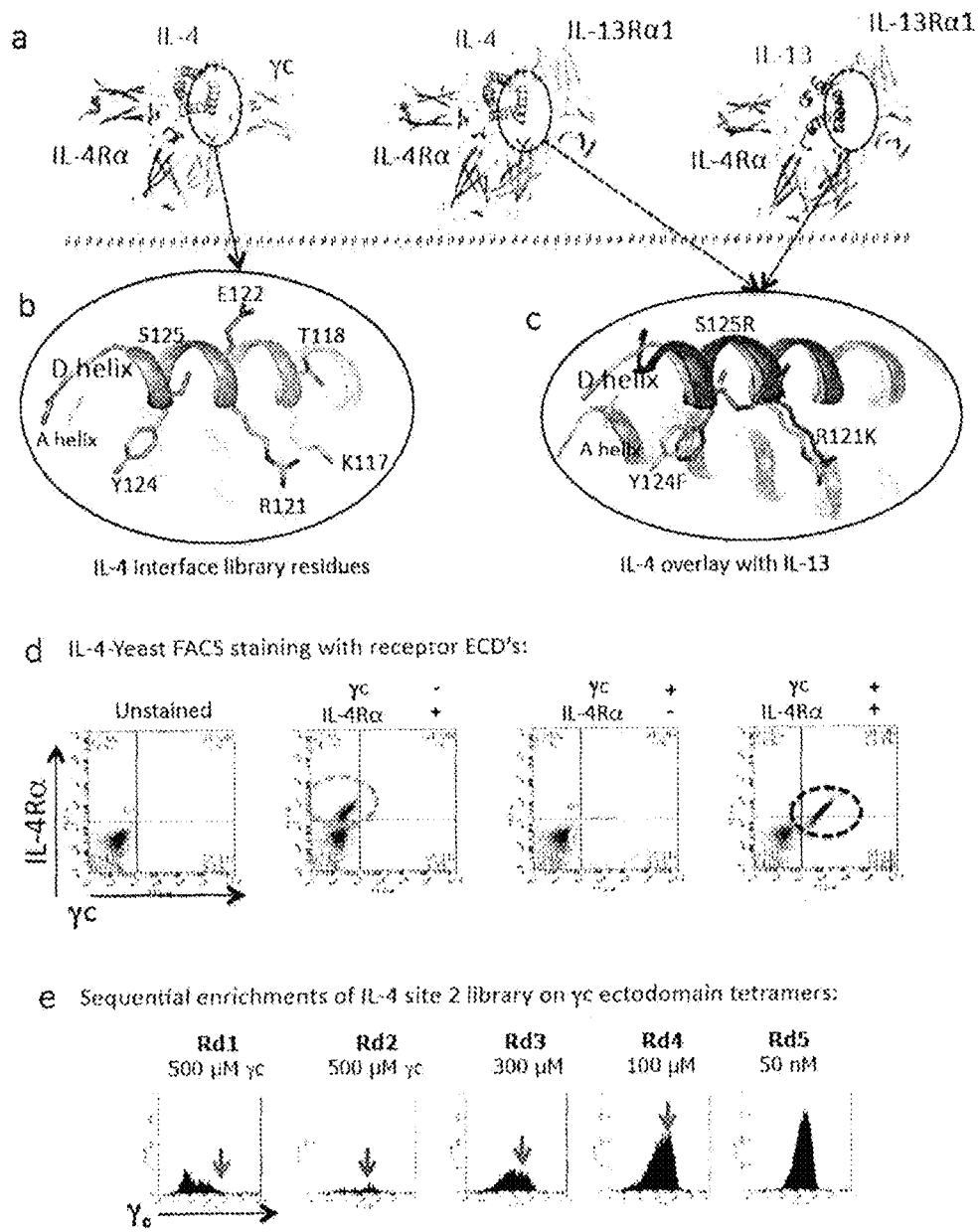
FIG. 1 depicts a structure-based engineering of IL-4 superkines. (a) Crystal structures of the IL-4 and IL-13 type I and type II ternary ectodomain complexes 6. (b) and (c) The principal γc and IL-13Rα1 binding sites on the D-helices of IL-4 and IL-13, respectively. In (b) the positions randomized in the IL-4 site 2 library are shown, and in (c) a structural superposition of IL-4 and IL-13 in the receptor complexes shows that positions 121, 124, and 125 of IL-4 superimpose closely on the analogous positions of IL-13, leading us to substitute these positions with those of IL-13. In (c) IL-13 is in purple, and IL-4 is in light green, substituted residues are in red. (d) Cooperative assembly of the IL-4/IL-4Rα/γc ternary ectodomain complex on yeast displaying IL-4. (e) Step-wise enrichment of the IL-4 site 2 library show in panel (b) by selection on γc tetramers. The library was complexed with IL-4Rα in the first step of selection, subsequent rounds did not include IL-4Rα. A final sixth round of selection was on γc monomer at 1 μm (not shown).

Many cytokines are being developed in the pharmaceutical sector for potential clinical applications. In the vast majority of these cases endogenous wild-type cytokines are being tried that are often associated with dose-limiting toxicities or inadequate efficacy.

One possibility for improving cytokines is to bias them for preferred activity on certain desired cell types. Cytokines which act through heterodimeric receptor complexes are particularly amenable to this approach. Protein engineering can be utilized to provide novel cytokine muteins which altered the relative affinity for shared receptors.

Accordingly, in some embodiments a method for selectively manipulating a cellular response in a target cell to a ligand recognized by two or more shared receptor polypeptides is provided. The method encompasses providing a mutein ligand, wherein the mutein ligand binds one of the two or more shared receptor polypeptides with higher affinity than the ligand. In other embodiments, the mutein ligand binds two of the two or more shared receptor polypeptides with higher affinity than the ligand and thereby selectively manipulating the cellular response. In still other embodiments, the mutein ligand binds one of the two or more shared receptor polypeptides with higher affinity and another one of the two or more shared receptor polypeptides with lower affinity than the ligand and thereby selectively manipulating the cellular response. In other embodiments, the two or more shared receptor polypeptides are not equally present on the target cell surface. In other embodiments, the shared receptor bound by the mutein ligand is present at lower levels on the target cell surface than the shared receptor not bound by the mutein ligand. In other embodiments, the shared receptor bound by the mutein ligand is present at higher levels on the target cell surface than the shared receptor not bound by the mutein ligand. The method of claim 1 wherein the shared receptor not bound by the mutein ligand has reduced accessibility to the mutein ligand. In other embodiments, accessibility to the shared receptor not bound by the mutein ligand is reduced by providing reagents that interfere with the accessibility of the shared receptor not bound by the mutein ligand. In other embodiments, the reagent is an antibody that recognizes the shared receptor not bound by the mutein ligand. In other embodiments, the mutein is an IL-4 mutein. In other embodiments, the shared receptor is common γ chain (γc) or interleukin-13 receptor alpha 1 (IL-13Rα1). In other embodiments, the higher affinity is at least 10-fold. In other embodiments, the lower affinity is at least 5-fold. In other embodiments, the ligand is a growth factor or a cytokine.

In some embodiments, a composition encompassing a cytokine mutein is provided wherein the cytokine mutein results in higher affinity binding to a shared cytokine receptor relative to the wild type cytokine. In some embodiments, the cytokine mutein results in a relative increase in the binding affinity with a first shared cytokine receptor and reduced binding affinity to a second shared cytokine receptor relative to the wild-type cytokine. In other embodiments, the cytokine mutein results in a relative increase in the binding affinity to two shared cytokine receptors relative to the wild-type cytokine. In some embodiments, the first shared cytokine receptor is expressed at lower levels than the second shared cytokine receptor, and in some embodiments, the first shared cytokine receptor is expressed at higher levels than the second shared cytokine receptor. In some embodiments, the cytokine mutein results in higher affinity binding to a first and a second shared cytokine receptor relative to a wild-type cytokine. In some embodiments, the increase in affinity if at least 10-fold. In some embodiments, the reduction in affinity is at least 5-fold.

In some embodiments, the shared cytokine receptor is common gamma chain ($\gamma_c$). In other embodiments, the shared cytokine receptor is IL-13 receptor α1. In some embodiments, the first shared cytokine receptor is γc and the second shared cytokine receptor is IL-13Rα1. In some embodiments, the first shared cytokine receptor is IL-13Rα1 and the second shared cytokine receptor is γc. In some embodiments, the first and second shared cytokine receptors are γc and IL-13Rα1.

In some embodiments, the cytokine mutein is an IL-4 mutein.

In some embodiments, IL-4 muteins with altered signaling properties are provided, wherein STAT phosphorylation is greater in Ramos cells contacted with the IL-4 mutein relative to Ramos cells contacted with the same concentration of IL-4, thereby demonstrating an IL-4 mutein with altered signaling properties. In some embodiments, an IL-4 mutein with altered signaling properties is provided, wherein STAT phosphorylation is greater in A549 cells contacted with the IL-4 mutein relative to A549 cells contacted with the same concentration of IL-4, thereby demonstrating an IL-4 mutein with altered signaling properties.

In some embodiments, an IL-4 mutein encompassing two, three, four, five, six, seven, or eight amino acid substitutions at positions 117, 118, 121, 122, 124, 125, 128, and 129 are provided, wherein the amino acid numbering is accordance with wild type human IL-4 (SEQ ID NO: 1.). In some embodiments, a substitution is made at position 121 of IL-4. In some embodiments, substitutions are made at positions 121 and 124 of IL-4. In other embodiments, substitutions are made at positions 121, 124, and 125.

In some embodiments, substitutions are made at positions 117, 118, 121, 122, 124, 125, 128, and 129 of IL-4. In other embodiments, a disclosed IL-4 mutein has the sequence 117R, 118V, 121Q, 122S, 124W, 125F, 128G, and 129A.

In some embodiments, a pharmaceutical composition is provided encompassing a cytokine mutein wherein administration of the mutein results in reduced side-effects relative to the wild-type mutein. In some embodiments, the side-effect is vascular leak syndrome. In other embodiments, a pharmaceutical composition is provided encompassing a cytokine mutein wherein the same therapeutic efficacy is achieved with less of the cytokine mutein relative to the wild-type mutein.

In some embodiments, a pharmaceutical composition is provided encompassing any one or more of the described cytokine muteins. In other embodiments, a method of treating a subject is provided, the method encompassing a composition of any one or more of the described cytokine muteins. In some embodiments, the subject is suffering from an inflammatory disease.

Further features and advantages will now be more particularly described in the following detailed description and claims.

DETAILED DESCRIPTION OF THE INVENTION

Introduction

Cytokines are broadly defined as molecules that are made by one cell and act on another. These molecules, also termed interleukins, interferons, growth factors, and TNFs, among other designations, are involved in essentially every important biological process, from cell proliferation to inflammation, immunity, migration, fibrosis, repair, and angiogenesis. Because of these properties, the use of cytokines as therapeutics has been explored. Unfortunately, in the vast majority of instances the use of wild-type cytokines as therapeutics is often associated with dose-limiting toxicities or inadequate efficacy.

Cytokines can be divided into two categories, Type I and Type II, based on three dimensional structure.

Type I cytokines have a four α-helical bundle structure, with an "up-up-down-down" configuration. These cytokines can be further divided into short-chain and long-chain four α-helical bundle cytokines on the basis of the length of the α-helices as well as some other structural/topological considerations. In the short-chain cytokines, the helices are typically 15 amino acids in length versus 25 amino acids for the long-chain cytokines.

In the short-chain cytokines, the AB loop is 'under' the CD loop, whereas it is "over" the CD loop in the long-chain cytokines. Another distinctive feature is that only short-chain cytokines have β-sheet structures within the AB and CD loops.

Examples of short chain cytokines are IL-2, IL-3, IL-4, IL-5, IL-7, IL-9, IL-13, IL-15, and IL-21, while examples long chain cytokines are IL-6, IL-11, and IL-12.

Type II cytokines have different structures. For example, interferon (IFN)-β has an extra helix in place of the CD strand, IFN-γ binds as an α-dimer of six helices/dimer, and IL-10 binds to its receptor as two sets of dimers, with each IL-10 domain consisting of six α-helices assembled from two intertwined peptide chains, with helices A-D being derived from one chain, and helices E and F derived from the twofold related chain.

Other Type II cytokines are IL-20 and IL-22.

Cytokines exert their function via interaction with specific receptors expressed on target cells. Like cytokines, cytokine receptors can be grouped into distinct families of related proteins based on structural similarities. These receptors fall into distinct families of related proteins and are sometimes classified into four broad groups. Type I cytokine receptors belong to the haematopoietin receptor family.

The type I cytokine receptors are multimeric in that they have an α receptor and one or two secondary components, which can be shared. Type I cytokine receptors can be divided into three sub-families based on the sharing of common receptor components. Type I cytokine receptors can either share a common β chain ($\beta_c$), gp130 or the common γ chain ($\gamma_c$).

Examples of cytokines that share $\beta_c$ are IL-3, IL-5, and GM-CSF; cytokines that share gp130 are for example, IL-6 and IL-11; and cytokines that share $\gamma_c$ are for example, IL-2, IL-3, IL-7, IL-9, IL-13, IL-15, and IL-21.

One possibility for improving cytokines is to bias them for preferred activity on certain desired cell types. The α receptor is responsible for cytokine specificity and cell specificity based on selective expression on the surface of different cell types. The shared receptors are also differentially expressed. Thus, the preferred activity of a cytokine on certain cell types can be engineered by manipulation of the ligand. For example, manipulation of the binding parameters for shared receptor recruitment could skew the activity of a cytokine towards certain cell types. This can be applied to a wide range of cytokines that signal through shared and/or heterodimeric receptors.

In order for the present invention to be more readily understood, certain terms and phrases are defined below as well as throughout the specification.

DEFINITIONS

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry are those well known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2$^{nd}$ ed. (1989) Cold Spring Harbor Laboratory Press, Cold Spring Harbor, N.Y., which is incorporated herein by reference), which are provided throughout this document. The nomenclature used herein and the laboratory procedures of analytical and synthetic organic chemistry described below are those well known and commonly employed in the art. Standard techniques, or modifications thereof, are used for chemical syntheses and chemical analyses.

By "wild type" or "WT" or "native" herein is meant an amino acid sequence or a nucleotide sequence that is found in nature, including allelic variations. "Wild type IL-4" means IL-4, whether native or recombinant, having the 129 normally occurring amino acid sequence of native human IL-4, SEQ ID NO:1 that does not include the 24 amino acid IL-4 signal peptide.

As used herein, "mutein" means a polypeptide wherein amino acid insertions, deletions, substitutions and modifications at one or more sites relative to a wild type polypeptide. Exemplary muteins can include substitutions of 1, 2, 3, 4, 5, 6, 7, 8, 9, 10 or more amino acids.

Muteins also include conservative modifications and substitutions throughout the wild type polypeptide or polynucleotide sequence (e.g., those that have a minimal effect on the secondary or tertiary structure of the mutein). Such conservative substitutions include those described by Dayhoff in *The Atlas of Protein Sequence and Structure* 5 (1978), and by Argos in *EMBO J.*, 8:779-785 (1989). For example, amino acids belonging to one of the following groups represent conservative changes: Group I: ala, pro, gly, gln, asn, ser, thr; Group II: cys, ser, tyr, thr; Group III:val, ile, leu, met, ala, phe; Group IV: lys, arg, his; Group V: phe, tyr, trp, his; and Group VI: asp, glu.

As used herein, "shared receptor polypeptides" refers to a polypeptide receptor that is shared between more than one ligand. Exemplary shared receptors are those bound by IL-4, which can include, but are not limited to, γc, gp130, βc, or IL-13Rα1.

As used herein, "ligand" refers to any molecule that is capable of specifically binding to another molecule, such as a receptor. The term "ligand" includes both agonists and antagonists, and can be, for example, a small molecule, an antibody fragment, siRNA, an antisense nucleic acid, a polypeptide such as a mutein, DNA, and/or RNA.

As used herein, "target cell" refers to a cell that expresses a shared receptor polypeptide or a cell expressing a receptor polypeptide capable of binding to the muteins of the present invention. Examples of target cells can include, but are not limited to, B-cells, CD4 T-cells, macrophages, monocytes, and epithelial cells.

"Numbered in accordance with wild type" means identifying a chosen amino acid with reference to the position at which that amino acid normally occurs in the mature sequence of a wild type polypeptide, for example 118 would refer to the hundred and eighteenth amino acid, that occurs in SEQ ID NO: 1.

The term "identity," as used herein in reference to polypeptide or DNA sequences, refers to the subunit sequence identity between two molecules. When a subunit position in both of the molecules is occupied by the same monomeric subunit (e.g., the same amino acid residue or nucleotide), then the molecules are identical at that position. The similarity between two amino acid or two nucleotide sequences is a direct function of the number of identical positions. In general, the sequences are aligned so that the highest order match is obtained. If necessary, identity can be calculated using published techniques and widely available computer programs, such as the GCS program package (Devereux et al., Nucleic Acids Res. 12:387, 1984), BLASTP, BLASTN, FASTA (Atschul et al., J. Molecular Biol. 215:403, 1990).

Sequence identity can be measured using sequence analysis software such as the Sequence Analysis Software Package of the Genetics Computer Group at the University of Wisconsin Biotechnology Center (1710 University Avenue, Madison, Wis. 53705), with the default parameters thereof.

The term "polypeptide," "protein" or "peptide" refer to any chain of amino acid residues, regardless of its length or post-translational modification (e.g., glycosylation or phosphorylation).

In the event the mutein polypeptides of the disclosure are "substantially pure," they can be at least about 60% by weight (dry weight) the polypeptide of interest. For example, the polypeptide can be at least about 75%, about 80%, about 85%, about 90%, about 95% or about 99%, by weight, the polypeptide of interest. Purity can be measured by any appropriate standard method, for example, column chromatography, polyacrylamide gel electrophoresis, or HPLC analysis.

The term "effective amount" as used herein refers to the amount necessary to elicit a desired biological response. The effective amount of a drug may vary depending on such factors as the desired biological endpoint, the drug to be delivered, the composition of any additional active or inactive ingredients, etc.

The term "expression" is used herein to mean the process by which a polypeptide is produced from DNA. The process involves the transcription of the gene into mRNA and the translation of this mRNA into a polypeptide. Depending on the context in which it is used, "expression" may refer to the production of RNA, protein, or both.

The term "gene product" as used herein means an RNA (for example, a messenger RNA (mRNA) or a micro RNA (miRNA)) or protein that is encoded by the gene.

As used herein, the term "isolated" refers to a molecule that is substantially pure. An isolated protein can be substantially pure, e.g., 60%, 65%, 70%, 75%, 80%, 85%, 90%, 95% or 99% free of other, different protein molecules.

As used herein, the terms "modulate" and "modulation" or "manipulate" and "manipulation" generally refer to the downregulation (e.g., inhibition or suppression), of specifically targeted genes (including their RNA and/or protein products), signaling pathways, cells, and/or a targeted phenotype, or the upregulation (e.g., induction or increase) of the targeted genes.

"Patient" or "subject" means a mammal, e.g. a human, who has or is at risk for developing a disease or condition such as an inflammatory disease, or has or is diagnosed as having an inflammatory disease, or could otherwise benefit from the compositions and methods described herein.

The term "reduce" and grammatical equivalents, as used herein, refers to any inhibition, reduction, decrease, suppression, downregulation, or prevention in expression or gene product activity. For example, the level of expression or activity can be, for example, 100% or less than 100%, for example, less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, or less than 5% of the uninhibited expression or activity.

The terms "treating" or "treatment" or "alleviation" or "amelioration" refer to both therapeutic treatment and prophylactic or preventative measures, wherein the object is to prevent or slow down (lessen) the targeted pathologic condition or disorder.

IL-4

IL-4 is a classical four α-helix bundle cytokine. Its primary binding chain is IL-4Rα, which is a type II cytokine receptor chain consisting of an extracellular domain, a transmembrane domain and a long intracellular tail, containing a Box1 domain, a binding site for PTB domain proteins- and three STAT6 docking and activation sites.

Wild-type human IL-4 comprises a 24 amino acid signal peptide and a 129 amino acid chain peptide. SEQ ID NO: 1 is the mature 129 amino acid human IL-4 sequence.

(SEQ ID NO: 1)
MGLTSQLLPPLFFLLACAGNFVHGHKCDITLQEIIKTLNSLTEQKTL

CTELTVTDIFAASKNTTEKETFCRAATVLRQFYSHHEKDTRCLGATA

QQFHRHKQLIRFLKRLDRNLWGLAGLNSCPVKEANQSTLENFLERLK

TIMREKYSKCSS.

The IL-4/IL-4Rα complex serves as a ligand for the second component of the IL-4 receptor, which for the Type-I receptor is γc and for the Type-II receptor, IL-13Rα1. Formation of the IL-4/IL-4Rα/γc or IL-4/IL-4Rα/IL-13Rα1 complex on the cell surface activates intracellular signaling pathways, including the Jak-STAT pathway and the PI3K/Akt pathway, the latter mobilized by recruitment of PTB domain proteins, notably IRS2. Recent solution of the crystal structures of extracellular domains of the IL-4-bound Type-I and Type-II IL-4 receptors (FIG. 1a) showed that IL-4 sits in the "Y-fork" formed by IL-4Rα and second receptor chain, and is in direct contact with the second receptor chain through binding surfaces on the D-helix of the cytokine.

The binding of IL-4 to IL-4Rα is very high affinity, with $K_D$ of ~$10^{-10}$ M. The subsequent binding of the IL-4/IL-4Rα complex to either γc or IL-13Rα1 is of relatively low affinity. Because of the very high affinity of binding of IL-4 to IL-4Rα, under most circumstances the formation of the signaling complex is determined by the relative level of expression of the second chain(s). Furthermore, the alternative second chains have different patterns of cellular expression with γc being mainly expressed on hematopoietic cells and IL-13Rα1 expressed mainly on non-hematopoietic cells, although some hematopoietic cells do express variable amounts of IL-13Rα1. Much of IL-4's regulatory activity is mediated by B cells and T cells that mainly express Type I receptors whereas much of its effector function, in which it mimics IL-13, is mediated by cells that uniquely express the Type-II receptor and that also respond to IL-13.

Functionally, IL-4 regulates Th2 differentiation of CD4 T-cells, immunoglobulin class switch to IgE and alternative macrophage activation by acting on naïve CD4 T-cells, B-cells and macrophages, respectively. Since IL-4 binds to the type II receptor, which is mainly expressed on non-hematopoietic cells, as efficiently as it binds to the type I receptor, it can induce effector functions as well as regulatory functions. Among the effector functions are airway hypersensitivity and goblet cell metaplasia. However, these latter activities are physiologically mainly induced by the Type-II receptor utilizing IL-13, since it is made in far larger amounts than IL-4. Further, since IL-13 cannot bind to the Type-I receptor that is dominantly expressed on hematopoietic cells, it has little or no "regulatory" activity. Overall, by using Type-I and Type-11 IL-4 receptors, IL-4 plays a central role in Th2-type inflammation, whether that is being triggered by an allergen or an invading extracellular parasite.

IL-4 is not currently in use as a therapeutic agent but it had been considered for such use in the past and, if free of toxicity, might be considered for purposes such as directing CD4 T cell differentiation during vaccination or altering an established pattern of differentiation in view of the recent recognition of the plasticity of differentiated CD4 T cells. In the early 1990's, clinical trials were performed in which IL-4 was administrated to cancer patients with the hope of boosting T-cell responses or of engaging the innate immune system.

However, intravenous administration of high dose (600 μg/m²/day) IL-4 resulted in a vascular leak syndrome in two out of three patients in the study group. Other toxicities were encountered in these studies and in preclinical analysis. While many of these toxicities involve IL-4 acting on non-hematopoietic cells, IL-4 does have substantial macrophage-mediated toxicity in mice. Administration of IL-4 to mice resulted in a hemophagocytic syndrome mediated by alternatively activated macrophages.

Utilization of IL-4 pharmacologically to regulate lymphocyte differentiation is complicated by its activity on non-hematopoietic cells through binding to the Type-II receptor and consequent effector function. Therefore production of IL-4 muteins that cannot activate the type II receptor or in which activation of the Type-I receptor can be achieved at substantially lower concentrations than activation of the Type-II receptor would be advantageous.

Accordingly, in some embodiments are provided engineered IL-4 muteins that have altered relative binding activities as compared to wild-type IL-4 for the second chains of Type-I and Type-II receptors. In some embodiments the IL-4 muteins modulate or enhance signaling, rather than block it.

Herein is described production of human IL-4 muteins, which are referred to as 'superkines,' that have a very high affinity for γc and diminished affinity for IL13Rα1, and conversely, those that bind with much higher affinity than IL-4 to IL-13Rα1, with little or no change in their affinity for γc.

Thus, in some embodiments, the IL-4 muteins have relatively high affinity for γc and diminished affinity for IL13Rα1. In other embodiments, the IL-4 muteins have relatively much higher affinity than IL-4 to IL-13Rα1, with little or no change in their affinity for γc.

IL-4 Superkines (Muteins)

In various embodiments, the present disclosure provides IL-4 mutant polypeptides, which may be, but are not necessarily, substantially purified and that can function as an agonist of wild-type IL-4; carrying out one or more of the biological activities of IL-4 (e.g., stimulation of cellular proliferation)).

An exemplary mutant IL-4 polypeptide includes an amino acid sequence that is at least about 80% identical to SEQ ID NO:1 which binds γc with an affinity that is greater than the affinity with which the polypeptide represented by SEQ ID NO: 1 binds the γc and diminished affinity for IL13Rα1. For example, a mutant IL-4 polypeptide can have at least one mutation (e.g., a deletion, addition, or substitution of 1, 2, 3, 4, 5, 6, 7, 8, 9, 10, 11, 12, 13, 14, 15, 16, 17, 18, 19, 20, or more amino acid residues) relative to a wild-type IL-4, and that binds the γc with greater affinity than the IL-4 of SEQ ID NO:1 and diminished affinity for IL13Rα1 as compared to that of SEQ ID NO.:1.

An exemplary mutant IL-4 polypeptide includes an amino acid sequence that is at least about 80% identical to SEQ ID NO:1 which binds with higher affinity than IL-4 (SEQ ID NO:1) to IL-13Rα1, with little or no change in the relative affinity for γc relative to the polypeptide of SEQ ID NO:1.

For example, a mutant IL-4 polypeptide can have at least one mutation (e.g., a deletion, addition, or substitution of 1, 2, 3, 4, 5, 6, 7, 8, 9, 10, 11, 12, 13, 14, 15, 16, 17, 18, 19, 20, or more amino acid residues) relative to a wild-type IL-4, and that binds with higher affinity than IL-4 (SEQ ID NO:1) to IL-13Rα1, with little or no change in the relative affinity for γc relative to the polypeptide of SEQ ID NO:1.

Exemplary mutant IL-4 polypeptides can be at least about 50%, 55%, 60%, 65%, 70%, 75%, 80%, 85%, 90%, 95%, 96%, 97%, 98%, 99% identical to wild-type IL-4. The mutation can consist of a change in the number or content of amino acid residues. For example, the mutant IL-4 can have a greater or a lesser number of amino acid residues than wild-type IL-4. Alternatively, or in addition, an exemplary mutant polypeptide can contain a substitution of one or more amino acid residues that are present in the wild-type IL-4. In various embodiments, the mutant IL-4 polypeptide can differ from wild-type IL-4 by the addition, deletion, or substitution of a single amino acid residue, for example, a substitution of the residue at position 121. Similarly, exemplary mutant IL-4 polypeptides can differ from wild-type by a substitution of two, three, four, five, six, seven, eight or more amino acid residues, for example, the residues at positions 117, 118, 21, 122, 124, 125, 128 and 129 of SEQ ID NO: 1.

By way of illustration, a polypeptide that includes an amino acid sequence that is at least 90% identical to a reference amino acid sequence of SEQ ID NO: 1 is a polypeptide that includes a sequence that is identical to the reference sequence except for the inclusion of up to 13 alterations of the reference amino acid of SEQ ID NO: 1. For example, up to 10% of the amino acid residues in the reference sequence may be deleted or substituted with another amino acid, or a number of amino acids up to 10% of the total amino acid residues in the reference sequence may be inserted into the reference sequence. These alterations of the reference sequence can occur at the amino (N--) or carboxy (C--) terminal positions of the reference amino acid sequence or anywhere between those terminal positions, interspersed either individually among residues in the reference sequence or in one or more contiguous groups within the reference sequence.

The substituted amino acid residue(s) can be, but are not necessarily, conservative substitutions, which typically include substitutions within the following groups: glycine, alanine; valine, isoleucine, leucine; aspartic acid, glutamic acid; asparagine, glutamine; serine, threonine; lysine, arginine; and phenylalanine, tyrosine.

For example, the substitution R121Q refers to a variant polypeptide, in this instance wherein the arginine at position 121 is replaced with glutamine. Also, a substitution can be made simply at position 74 within the parent polypeptide, for example 121Q would refer to the substitution of the amino acid at position 121 with glutamine, irrespective of the amino acid occurring at position 121 of the parent polypeptide.

By "protein variant" or "variant protein" or "variant polypeptide" herein is meant a protein that differs from a wild-type protein by virtue of at least one amino acid modification. The parent polypeptide may be a naturally occurring or wild-type (WT) polypeptide, or may be a modified version of a WT polypeptide. Variant polypeptide may refer to the polypeptide itself, a composition comprising the polypeptide, or the amino sequence that encodes it. Preferably, the variant polypeptide has at least one amino acid modification compared to the parent polypeptide, e.g. from about one to about ten amino acid modifications, and preferably from about one to about five amino acid modifications compared to the parent.

By "parent polypeptide", "parent protein", "precursor polypeptide", or "precursor protein" as used herein is meant an unmodified polypeptide that is subsequently modified to generate a variant. A parent polypeptide may be a wild-type polypeptide, or a variant or engineered version of a wild-type polypeptide. Parent polypeptide may refer to the polypeptide itself, compositions that comprise the parent polypeptide, or the amino acid sequence that encodes it.

With respect to affinity, herein are disclosed exemplary mutant IL-4 polypeptides that bind the $\gamma_c$ with an affinity that is higher than the wild type IL-4 polypeptide by at least about 2%, at least about 5%, at least about 10%, at least about 20%, at least about 30%, or at least about 40% higher affinity or more. The wild-type IL-4 polypeptide binds the $\gamma_c$ with a Kd of about 3300 nM. The binding affinity of exemplary disclosed mutant IL-4 polypeptides can also be expressed as 1.2, 1.4, 1.5, 2, 5, 10, 15, 20, 25, 50, 100, 200, 250, 500, 1000, 1500, 2000, 2500, 3000, 3500 or more fold higher affinity for $\gamma_c$ than wild-type IL-4.

Exemplary mutant IL-4 polypeptides can have the ability to exhibit an increased association rate with the $\gamma_c$ receptor subunit.

Also provided in the instant disclosure are mutant IL-4 polypeptides that bind the $\gamma_c$ with an affinity that is lower than the wild type IL-4 polypeptide by at least about 2%, at least about 5%, at least about 10%, at least about 20%, at least about 30%, or at least about 40% lower affinity or more. The binding affinity of exemplary disclosed mutant IL-4 polypeptides can also be expressed as 1.2, 1.4, 1.5, 2, 3, 4, 5, 10, 15, 20, or more fold lower affinity for the $\gamma_c$ than wild-type IL-4.

With respect to affinity, herein are disclosed exemplary mutant IL-4 polypeptides that bind the IL-13Rα1 with an affinity that is higher than the wild type IL-4 polypeptide by at least about 2%, at least about 5%, at least about 10%, at least about 20%, at least about 30%, or at least about 40% higher affinity or more. The wild-type IL-4 polypeptide binds the IL-13Rα1 with a Kd of about 4200 nM. The binding affinity of exemplary disclosed mutant IL-4 polypeptides can also be expressed as 1.2, 1.4, 1.5, 2, 5, 10, 15, 20, 25, 50, 100, 200, 250, 400, 450, 500, 1000, 1500, 2000 or more fold higher affinity for the IL-13Rα1 than wild-type IL-4.

Exemplary mutant IL-4 polypeptides can have the ability to exhibit an increased association rate with the IL-13Rα1 receptor subunit.

Also provided in the instant disclosure are mutant IL-4 polypeptides that bind the IL-13Rα1 with an affinity that is lower than the wild type IL-4 polypeptide by at least about 2%, at least about 5%, at least about 10%, at least about 20%, at least about 30%, or at least about 40% lower affinity or more. The binding affinity of exemplary disclosed mutant IL-4 polypeptides can also be expressed as 1.2, 1.4, 1.5, 2, 3, 4, 5, 10, 15, 20, or more fold lower affinity for the IL-13Rα1 than wild-type IL-4.

Exemplary mutant IL-4 polypeptides possessing both properties of increased affinity for the $\gamma_c$ and decreased affinity for IL-13Rα1 as compared to wild-type IL4 are also disclosed.

Exemplary mutant IL-4 polypeptides possessing both properties of increased affinity for the $\gamma_c$ and IL-13Rα1 as compared to wild-type IL4 are also disclosed.

Exemplary mutant IL-4 polypeptides possessing both properties of decreased affinity for the $\gamma_c$ and increased affinity for IL-13Rα1 as compared to wild-type IL4 are also disclosed.

Diseases Associated with Cytokines

Disorders of Proliferation and Differentiation

In some embodiments, mutant cytokine polypeptides, and/or nucleic acids expressing them, can be administered to a subject to treat a disorder associated with abnormal apoptosis or a differentiative process (e.g., cellular proliferative disorders or cellular differentiative disorders, such as cancer, for example).

As used herein, the terms "cancer" (or "cancerous"), "hyperproliferative," and "neoplastic" refer to cells having the capacity for autonomous growth (e.g., an abnormal state or condition characterized by rapidly proliferating cell growth). Hyperproliferative and neoplastic disease states may be categorized as pathologic (e.g., characterizing or constituting a disease state), or they may be categorized as non-pathologic (e.g., as a deviation from normal but not associated with a disease state). The terms are meant to include all types of cancerous growths or oncogenic processes, metastatic tissues or malignantly transformed cells, tissues, or organs, irrespective of histopathologic type or stage of invasiveness.

Examples of cancers include, without limitation carcinomas, sarcomas, and hematopoietic neoplastic disorders, e.g., leukemia).

The mutant cytokine polypeptides can be used to treat patients who have, who are suspected of having, or who may be at high risk for developing any type of cancer, including renal carcinoma or melanoma, or any viral disease. Exemplary carcinomas include those forming from tissue of the cervix, lung, prostate, breast, head and neck, colon and ovary. The term also includes carcinosarcomas, which include malignant tumors composed of carcinomatous and sarcomatous tissues.

As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias (e.g., erythroblastic leukemia and acute megakaryoblastic leukemia). Additional exemplary myeloid disorders include, but are not limited to, acute promyeloid leukemia (APML), acute myelogenous leukemia (AML) and chronic myelogenous leukemia (CML) (reviewed in Vaickus, L. (1991) Crit Rev. in Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM).

Additional forms of malignant lymphomas include, but are not limited to non-Hodgkin lymphoma and variants thereof, peripheral T cell lymphomas, adult T cell leukemia/lymphoma (ATL), cutaneous T cell lymphoma (CTCL), large granular lymphocytic leukemia (LGF), Hodgkin's disease and Reed-Stemberg disease.

Other examples of proliferative and/or differentiative disorders include skin disorders. The skin disorder may involve the aberrant activity of a cell or a group of cells or layers in the dermal, epidermal, or hypodermal layer, or, an abnormality in the dermal-epidermal junction.

For example, the skin disorder may involve aberrant activity of keratinocytes (e.g., hyperproliferative basal and immediately suprabasal keratinocytes), melanocytes, Langerhans cells, Merkel cells, immune cell, and other cells found in one or more of the epidermal layers, e.g., the stratum basale (stratum germinativum), stratum *spinosum*, stratum *granulosum*, stratum lucidum or stratum corneum.

In other embodiments, the disorder may involve aberrant activity of a dermal cell, for example, a dermal endothelial, fibroblast, immune cell (e.g., mast cell or macrophage) found in a dermal layer, for example, the papillary layer or the reticular layer.

Examples of skin disorders include psoriasis, psoriatic arthritis, dermatitis (eczema), for example, exfoliative dermatitis or atopic dermatitis, *pityriasis rubra* pilaris, *pityriasis* rosacea, parapsoriasis, *pityriasis* lichenoiders, lichen planus, lichen *nitidus*, ichthyosiform dermatosis, keratodermas, dermatosis, alopecia areata, pyoderma gangrenosum, vitiligo, pemphigoid (e.g., ocular cicatricial pemphigoid or bullous pemphigoid), urticaria, prokeratosis, rheumatoid arthritis that involves hyperproliferation and inflammation of epithelial-related cells lining the joint capsule; dermatitises such as seborrheic dermatitis and solar dermatitis; keratoses such as seborrheic keratosis, senile keratosis, actinic keratosis, photo-induced keratosis, and keratosis follicularis; acne vulgaris; keloids and prophylaxis against keloid formation; nevi; warts including verruca, condyloma or condyloma *acuminatum*, and human papilloma viral (HPV) infections such as venereal warts; leukoplakia; lichen planus; and keratitis. The skin disorder can be dermatitis, e.g., atopic dermatitis or allergic dermatitis, or psoriasis.

Alternatively, or in addition to methods of direct administration to patients, in some embodiments, mutant cytokine polypeptides can be used in ex vivo methods. For example, cells (e.g., peripheral blood lymphocytes or purified populations of lymphocytes isolated from a patient and placed or maintained in culture) can be cultured in vitro in culture medium and the contacting step can be affected by adding the cytokine mutant to the culture medium. The culture step can include further steps in which the cells are stimulated or treated with other agents, e.g., to stimulate proliferation, or to expand a population of cells that is reactive to an antigen of interest (e.g., a cancer antigen or a viral antigen). The cells are then administered to the patient after they have been treated.

Pulmonary Disorders

Pathologic conditions amenable to amelioration with the disclosed cytokine mutein compositions and methods of their use include, for example, pulmonary disorders such as asthma and allergic inflammatory responses.

Features of asthma, for example, include recurrent episodes of respiratory symptoms; variable airflow obstruction that is often reversible, either spontaneously or with treatment; presence of airway hyper-reactivity; and chronic airway inflammation in which many cells and cellular elements, including, for example, mast cells, eosinophils, T lymphocytes, macrophages, neutrophils, and epithelial cells, are involved (see National Heart, Lung, and Blood Institute: National Asthma Education and Prevention Program. Expert Panel Report Guidelines for the diagnosis and management of asthma. *J. Allergy Clin. Immunol.* 88:425-534, 1991; National Heart, Lung, and Blood Institute National Asthma Education Program Expert Panel Report II: Guidelines for the diagnosis and management of asthma; 1997. NIH Publication No. 97-4051A) While all of these features need not be present in any given asthmatic patient, and an absolute "minimum criteria" to establish a diagnosis of asthma has not been or widely agreed upon, the presence of airway hyper-reactivity is a common finding in patients with current symptoms and active asthma.

Airway hyperresponsiveness is a characteristic feature of asthma and consists of an increased sensitivity of the airways to an inhaled constrictor agonist, a steeper slope of the dose-response curve, and a greater maximal response to the agonist (Byrne and Inman, Chest, 2003). Measurements of airway responsiveness are useful in making a diagnosis of asthma, particularly in patients who have symptoms that are consistent with asthma and who have no evidence of airflow obstruction. Certain inhaled stimuli, including, for example, environmental allergens, increase airway inflammation and enhance airway hyperresponsiveness. The changes in airway hyperresponsiveness in healthy subjects are of much smaller magnitude than those seen when asthmatic patients with persistent airway hyperresponsiveness. The pathogenesis of asthma, and amelioration due to treatment according to the present methods, can be followed by bronchoscopy, bronchoalveolar lavage, airway biopsy, measurement of airway gases, and other such methods known to the skilled clinician.

Formulations

One or more therapeutic agent, alone or in combination with one or more chemotherapeutic agents, can be formulated with a pharmaceutically acceptable carrier for administration to a subject. The active ingredients can be formulated alone (individually) for sequential administration or may be formulated together for concurrent administration.

The term "pharmaceutically acceptable carrier" as used herein means one or more compatible solid or liquid filler, diluents or encapsulating substances which are suitable for administration to a subject. The components of the pharmaceutical compositions also are capable of being commingled with each other, in a manner such that there is no interaction, which would substantially impair the desired pharmaceutical efficiency. Such preparations may routinely contain pharmaceutically acceptable concentrations of salt, buffering agents, preservatives, compatible carriers, adjuvants and optionally other therapeutic ingredients.

The compositions described herein may be administered as a free base or as a pharmaceutically acceptable salt. Such pharmacologically and pharmaceutically acceptable salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene sulphonic, and benzene sulphonic. Also, pharmaceutically acceptable salts can be prepared as alkaline metal or alkaline earth salts, such as sodium, potassium or calcium salts of the carboxylic acid group.

The pharmaceutical compositions also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Suitable liquid or solid pharmaceutical preparation forms are, for example, aqueous or saline solutions for inhalation, microencapsulated, encochleated, coated onto microscopic gold particles, contained in liposomes (including pH-dependent release formulations), lipidoids, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of the compositions, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, Science 249:1527-1533, 1990 and Langer and Tirrell, Nature, 2004 Apr. 1; 428(6982): 487-92.

The compositions may conveniently be presented in unit dosage form and may be prepared by any of the methods well known in the art of pharmacy. In certain embodiments, the composition that is administered is in powder or particulate form rather than as a solution. Examples of particulate forms contemplated as part of the invention are provided in U.S. 2002/0128225. In some embodiments, the compositions are administered in aerosol form. In other embodiments, the compositions may be in powder form for constitution with a suitable vehicle, e.g., sterile pyrogen-free water, before use.

In addition, the compositions described herein may be formulated as a depot preparation, time-release, delayed release or sustained release delivery system. Such systems can avoid repeated administrations of the compositions described herein, increasing convenience to the subject and the physician. Such long acting formulations may be formulated with suitable polymeric or hydrophobic materials (for example as an emulsion in an acceptable oil) or ion exchange resins, or as sparingly soluble derivatives, for example, as a sparingly soluble salt.

Many types of release delivery systems are available and known to those of ordinary skill in the art. They include polymer based systems such as polylactic and polyglycolic acid, beta-glucan particles, polyanhydrides and polycaprolactone; nonpolymer systems that are lipids including sterols such as cholesterol, cholesterol esters and fatty acids, neutral fats such as mono-, di- and triglycerides or lipidoids; hydrogel release systems; silastic systems; peptide based systems; wax coatings, compressed tablets using conventional binders and excipients, partially fused implants and the like. In addition, a pump-based hardware delivery system can be used, some of which are adapted for implantation.

Controlled release can also be achieved with appropriate excipient materials that are biocompatible and biodegradable. These polymeric materials which effect slow release may be any suitable polymeric material for generating particles, including, but not limited to, non-biodegradable/non-biodegradable and biodegradable/biodegradable polymers. Such polymers have been described in great detail in the prior art and include, but are not limited to: beta-glucan particles, polyamides, polycarbonates, polyalkylenes, poly-alkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulfate sodium salt, poly (methyl methacrylate), poly (ethylmethacrylate), poly(butylmethacrylate), poly(isobutylmethacrylate), poly(hexylmethacrylate), poly (isodecylmethacrylate), poly(lauryl methacrylate), poly (phenyl methacrylate), poly(methyl acrylate), poly(isopropyl acrylate), poly(isobutyl acrylate), poly(octadecyl acrylate), polyethylene, polypropylene poly(ethylene glycol), poly(ethylene oxide), poly(ethylene terephthalate), poly(vinyl alcohols), poly(vinyl acetate, poly vinyl chloride polystyrene, polyvinylpyrrolidone, hyaluronic acid, and chondroitin sulfate. In one embodiment the slow release polymer is a block copolymer, such as poly(ethylene glycol) (PEG)/poly(lactic-co-glycolic acid) (PLGA) block copolymer.

Examples of non-biodegradable polymers include ethylene vinyl acetate, poly(meth) acrylic acid, polyamides, copolymers and mixtures thereof.

Examples of biodegradable polymers include synthetic polymers, for example, beta-glucan particles, polymers of lactic acid and glycolic acid, polyanhydrides, poly(ortho) esters, polyurethanes, poly(butic acid), poly(valeric acid), poly(caprolactone), poly(hydroxybutyrate), poly(lactide-co-glycolide) and poly(lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. The foregoing materials may be used alone, as physical mixtures (blends), or as copolymers. Preferred polymers are polyesters, polyanhydrides, polystyrenes and blends thereof.

Effective amounts of the compositions described herein are administered to a subject in need of such treatment. Effective amounts are those amounts, which will result in a desired improvement in the condition, disease or disorder or symptoms of the condition, disease or disorder.

Effective doses range from 1 ng/kg to 100 mg/kg body weight, or from 100 ng/kg to 50 mg/kg body weight, or from 1 µg/kg to 10 mg/kg body weight, depending upon the mode of administration. Alternatively, effective doses can range from 3 micrograms to 14 milligrams per 4 square centimeter area of cells. The absolute amount will depend upon a variety of factors (including whether the administration is in conjunction with other methods of treatment, the number of doses and individual patient parameters including age, physical condition, size and weight) and can be determined with routine experimentation. One useful dose that can be is the highest safe dose according to sound medical judgment.

The time between the delivery of the various active agents can be defined rationally by first principles of the kinetics, delivery, release, agent pharmacodynamics, agent pharmacokinetics, or any combination thereof. Alternatively, the time between the delivery of the various agents can be defined empirically by experiments to define when a maximal effect can be achieved.

Mode of Administration

The mode of administration may be any medically acceptable mode including oral administration, sublingual administration, intranasal administration, intratracheal administration, inhalation, ocular administration, topical administration, transdermal administration, intradermal administration, rectal administration, vaginal administration, subcutaneous administration, intravenous administration, intramuscular administration, intraperitoneal administration, intrasternal, administration, or via transmucosal administration. In addition, modes of administration may be via an extracorporeal device and/or tissue-penetrating electro-magnetic device.

The particular mode selected will depend upon the particular active agents selected, the desired results, the particular condition being treated and the dosage required for therapeutic efficacy. The methods described herein, generally speaking, may be practiced using any mode of administration that is medically acceptable, for example, any mode that produces effective levels of inflammatory response alteration without causing clinically unacceptable adverse effects.

The compositions can be provided in different vessels, vehicles or formulations depending upon the disorder and mode of administration. For example, for oral application, the compositions can be administered as sublingual tablets, gums, mouth washes, toothpaste, candy, gels, films, etc.; for ocular application, as eye drops in eye droppers, eye ointments, eye gels, eye packs, as a coating on a contact lens or an intraocular lens, in contacts lens storage or cleansing solutions, etc.; for topical application, as lotions, ointments, gels, creams, sprays, tissues, swabs, wipes, etc.; for vaginal or rectal application, as an ointment, a tampon, a suppository, a mucoadhesive formulation, etc.

The compositions, may be administered by injection, e.g., by bolus injection or continuous infusion, via intravenous, subcutaneous, intramuscular, intraperitoneal, intrasternal routes. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. For oral administration, the compositions can be formulated readily by combining the compositions with pharmaceutically acceptable carriers well known in the art, e.g., as a sublingual tablet, a liquid formulation, or an oral gel.

For administration by inhalation, the compositions may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compositions and a suitable powder base such as lactose or starch. Medical devices for the inhalation of therapeutics are known in the art. In some embodiments the medical device is an inhaler. In other embodiments the medical device is a metered dose inhaler, diskhaler, Turbuhaler, diskus or a spacer. In certain of these embodiments the inhaler is a Spinhaler (Rhone-Poulenc Rorer, West Mailing, Kent). Other medical devices are known in the art and include Inhale/Pfizer, Mannkind/Glaxo and Advanced Inhalation Research/Alkermes.

The compositions may also be formulated in rectal or vaginal compositions such as suppositories or retention enemas, e.g., containing conventional suppository bases such as cocoa butter or other glycerides.

Additional Uses

The muteins described herein can be labeled directly or indirectly with a moiety that is a label or produces a signal, e.g., an enzyme, a radiolabel, an epitope, or a fluorescent protein (such as green fluorescent protein). The muteins described herein can be contacted to a sample or to cells to determine if a receptor is present in the sample or on the cells, e.g., using standard immunoblotting, immunofluorescence, enzyme immunoassay (EIA), radioimmunoassay (RIA), fluorescence energy transfer, Western blot, and other diagnostic and detection techniques.

The muteins described herein can also be labeled for in vivo detection and administered to a subject. The subject can be imaged, e.g., by NMR or other tomographic means. For example, the binding agent can be labeled with a radiolabel such as $^{131}$I, $^{111}$In, $^{131}$I, $^{99m}$Tc, $^{32}$P, $^{125}I$, $^{3}H$, $^{14}C$, and $^{188}Rh$, fluorescent labels such as fluorescein and rhodamine, nuclear magnetic resonance active labels, positron emitting isotopes detectable by a positron emission tomography ("PET") scanner, chemiluminescers such as luciferin, and enzymatic markers such as peroxidase or phosphatase. The muteins described herein can be labeled with a contrast agent such as paramagnetic agents and ferromagnetic or superparamagnetic agents.

The muteins described herein can be coupled to a radioactive isotope such as an α, β, or γ-emitter. Examples of radioactive isotopes include iodine ($^{131}I$ or $^{125}I$), yttrium ($^{90}Y$), lutetium ($^{177}Lu$), actinium ($^{225}Ac$), praseodymium, or bismuth ($^{212}Bi$ or $^{213}Bi$). The binding protein can be coupled to a biological protein, a molecule of plant or bacterial origin (or derivative thereof), e.g., a maytansinoid (e.g., maytansinol, an analog thereof or DM1), as well as a taxane (e.g., taxol or taxotere), or a calicheamicin. Examples of maytansinol analogues include those having a modified aromatic ring (e.g., C-19-decloro, C-20-demethoxy, C-20-acyloxy) and those having modifications at other positions (e.g., C-9-CH, C-14-alkoxymethyl, C-14-hydroxymethyl or aceloxymethyl, C-15-hydroxy/acyloxy, C-15-methoxy, C-18-N-demethyl, 4,5-deoxy). Maytansinol and maytansinol analogues are described, for example, in U.S. Pat. No. 6,333,410. Maytansinol can be coupled using, e.g., an N-succinimidyl 3-(2-pyridyldithio)proprionate (also known as N-succinimidyl 4-(2-pyridyldithio)pentanoate or SPP), 4-succinimidyl-oxycarbonyl-a-(2-pyridyldithio)-toluene (SMPT), N-succinimidyl-3-(2-pyridyldithio)butyrate (SDPB), 2-iminothiolane, or S-acetylsuccinic anhydride.

The following examples are provided by way of illustration only and are not meant to limit the scope of the invention. Those of skill in the art will readily recognize a variety of non-critical parameters that could be changed or modified to yield essentially similar results.

EXAMPLES

Example 1: Development of IL-4 Muteins with Altered Binding Affinities

The IL-4/IL-13 system was used to test the concept that manipulation of relative affinities for a shared cytokine receptor can produce cytokines with distinctive patterns of reactivity. Two approaches were taken to engineer IL-4 for higher affinity binding to $\gamma_c$ (FIG. 1*b*) or IL-13Rα1 (FIG. 1*c*)

The three dimensional structures of the complete liganded Type-I and Type II receptor ternary complexes have recently been solved. IL-13 binds with relatively higher affinity to IL-13Rα1 than IL-4 (KD 30 nM versus KD>1 μM). Thus, the structures of IL-4 and IL-13 were aligned from their structures in the two type II ternary complexes (IL-4/IL-4Rα/IL-13Rα1 and IL-13/IL-4Rα/IL-13Rα1).

The D helices of IL-4 and IL-13, which form extensive contacts with IL-13Rα1, align very closely in the respective complexes. Three IL-4 D helix residues, R121, Y124, and S125, that form contacts with γc in the IL-4 Type-II receptor ternary complex, differ from those in IL-13. These residues were therefore swapped for their IL-13 positional equivalents (FIG. 1c) and two IL-4 variants were made, a conservative double mutant, R121K, Y124F, referred to as KF, and a triple mutant, KFR, in which all three residues are swapped R121K, Y124F, and S125R.

To increase the affinity of IL-4 for γc, a combinatorial library approach was applied utilizing yeast surface display for affinity maturation. IL-4 was fused to the yeast surface protein Aga2p, where it was recognized by the IL-4 receptor ectodomains (ECD) (FIG. 1d). To accomplish this, human IL-4 DNA was cloned into yeast display vector pCT302, forming the pCT302_IL-4 vector. S. cerevisiae strain EBY100 was transformed with the pCT302_IL-4 vector and grown for 3 days at 30° C. on SDCAA plates. Individual colonies of IL-4 yeast were grown overnight at 30° C. in SDCAA liquid media (pH 4.5), followed by induction in SGCAA liquid media (pH 7.0) for 2 days at 20° C.

C-terminally biotinylated ectodomains of IL-4Rα, γc, and IL-13Rα1 were produced for use as staining and sorting reagents for tetramer selection by coupling to streptavidin. Yeast were stained with biotinylated IL-4Rα(b-IL-4Rα), tetramerized biotinylated γc (b-γc), or b-γc in the presence of b-IL-4Rα. Highest concentration γc tetramers were formed by incubating 2 μM b-γc with 470 nM SAV-PE (streptavidin-phycoerythrin conjugate, Invitrogen) for 15 min on ice. Analysis was performed on an Accuri® C6 flow cytometer system.

IL-4 displayed on yeast bound IL-4Rα with high affinity (FIG. 1d, second panel), but did not bind to γc in the absence of IL-4Rα(FIG. 1d, third panel). In the presence of IL-4Rα, IL-4 on yeast binds to the γc extracellular domain tetramer, indicating cooperative assembly of the heterodimeric receptor complex (FIG. 1d, far right panel). These experiments demonstrate sequential engagement of wild-type IL-4 site 1 and site 2 on the yeast by IL-4Rα and γc, respectively.

To create a library of the D helix of IL-4, which is the principal γc-interacting helix of the cytokine (FIG. 1b), the IL-4/γc interface in the crystal structure of the Type-I receptor ternary complex was analyzed. Based on the interatomic contacts, a focused library was created in which eight residues on the face of helix D were randomized to the degenerate codon NNK (N=A,C,G or T; K=G or T), which allows utilization of any of the 20 amino acids (FIG. 1b). Using assembly PCR, a yeast library with 2×10$^8$ variants was created, representing about 1% of the full theoretical diversity (2.6×10$^{10}$).

Assembly PCR was done using 11 overlapping primers one of which contained the randomized sequence. The PCR product was further amplified using the primers 5'CTAGTG-GTGGTGGTGGTTCTGGTGGTGGTGGTTCTGGTG-GTGGTGGTTCTGC TAGCCACAAGTGCGATATCAC-CTTAC 3' (SEQ ID NO:2) and 5'CAGATCTCGAGCAAGTCTTCTTCGGAGA-TAAGCTTTTGTTCGCCACCAGAG GATCC 3' (SEQ ID NO:3), which also contained the necessary vector sequence homology for homologous recombination inside the yeast. Insert DNA was combined with linearized vector backbone and electrocompetent EBY100, electroporated, and rescued, as previously described. The electroporations yielded a library of 2×10$^8$ transformants.

Selections were performed using magnetic activated cell sorting (MACS, Miltenyi). The first round of selection was performed with 2×10$^9$ cells from the yeast library, approximately 10-fold coverage of the number of transformants. Subsequent rounds of selection used 1×10$^7$ yeast cells.

Selections were carried out by decorating the yeast library with IL-4Rα to create the IL-4/IL4Rα site 2 on the yeast, and then enriched γc-binding yeast using magnetic activated cell sorting (MACS) through five rounds of in vitro selection (FIG. 1e). The initial round selected yeast that bound to tetrameric γc in the presence of IL-4Rα. Consecutive selection rounds (two through five) were performed by decreasing the concentration of tetrameric γc with the final selection, a sixth round, using 1 μM concentration of monomeric γc. High avidity tetramers of γc were essential for the detection of relatively weak γc binding and early rounds of selection. Subsequent rounds of selection used 1×10$^7$ yeast cells. IL-4 libraries were grown fresh overnight at 30° C. in SDCAA liquid media (pH 4.5), followed by induction in SGCAA liquid media (pH 7.0) for 2 days at 20° C. The yeast were stained with biotinylated IL-4Rα(b-IL-4Rα), tetramerized biotinylated γc (b-γc), or b-γc in the presence of b-IL-4Rγ with a buffer solution of 1×PBS and 0.5% BSA for 2 hrs at 4 C. Tetramers of γc were formed by incubating 2 μM b-γc with 470 nM SAV-PE (streptavidin-phycoerythrin conjugate, Invitrogen) for 15 min on ice. Monomeric selection with γc was done through sequential binding of γc, 2 μg/mL SA-PE, and 50 μl Miltenyi anti-PE microbeads/1× 10$^8$ yeast cells. Analysis was performed on an Accuri C6 flow cytometer.

Sequencing the IL-4-selected variants revealed two unique sequences, the 'RQ' and 'RGA' variants, in which one, RGA, was highly enriched (Table 1). RQ contained only a single residue deviation from wild-type IL-4, R121Q. Interestingly, Q at this position is present in the majority of γc binding cytokines. The other selected cytokine, RGA, contained the R121Q mutation together with 7 other changes in helix D (see Table 1 for sequences of RQ and RGA).

Example 2: Second Receptor Chain Binding Characteristics of the IL-4 Muteins

The binding characteristics of the resulting IL-4 muteins were characterized. Recombinant IL-4 and the variants KF, KFR, RQ and RGA using baculovirus and formed complexes with IL-4Rα in order to measure their site 2 binding affinities and kinetics for IL-13Rα1 and γc by surface plasmon resonance (SPR) (see Table 1 and FIG. 2).

Human IL-4 variants (amino acids 1-129), the IL-4Rα ectodomain (amino acids 1-202), IL-13Rα1 (amino acids 1-310), and γc (amino acids 34-232) were cloned into the pAcGP67A vector (BD Biosciences) in frame with an N-terminal gp67 signal sequence and C-terminal hexahistidine tag and produced using the baculovirus expression system. Baculovirus stocks were prepared by transfection and amplification in Spodoptera frugiperda (Sf9) cells grown in SF900II media (Invitrogen), and protein expression was carried out in suspension Trichoplusia ni (HiFive) cells grown in Insect-Xpress™ media (Lonza). Proteins were expressed and captured from HiFive supernatants after 48-60 h by nickel agarose (Qiagen), concentrated and purified by size exclusion chromatography on a Superdex™ 200 column (GE Healthcare), equilibrated in 10 mM HEPES (pH 7.2) and 150 mM NaCl. IL-4 variants used in cell based assays were expressed fully glycoslylated. The high affinity binary complexes (IL-4Rα with IL-4 variants) used in SPR measurements were coexpressed and fully glycosylated. For biotinylated receptor expression, IL-4Rα, IL-13Rα1, and γc were cloned into the pAcGP67-A vector with a C-terminal biotin acceptor peptide (BAP)LNDIFEAQKIEWHE and hexahistidine tag. Receptor proteins were coexpressed with BirA ligase with excess biotin (100 μM). For crystallization, discussed below, IL-4 RGA was co-expressed with γc with the N-linked glycosylation site Asn53 mutated to Gln. After nickel purification, the crystallization proteins were treated overnight with carboxypeptidase-A followed by size exclusion. Protein was concentrated to 8-20 mg/mL for crystallization.

Surface plasmon resonance experiments were conducted on a Biacore T100 instrument. Protein concentrations were quantified by UV spectroscopy at 280 nm using a Nanodrop2000 spectrometer (Thermo Scientific). All data was analyzed using the Biacore T100 evaluation software version 2.0 with a 1:1 Langmuir binding model. Experiments used a Biacore SA sensor chip (GE Healthcare). Biotinylated receptors were captured at a low density (100-200 RU) and kinetic runs were conducted at 40 μL/min. An unrelated biotinylated protein was immobilized as a reference surface for the SA sensor chip with matching RU to the experimental surface. All measurements were made using 3-fold serial dilution of IL-4 variants in the running buffer (1×HBS-P (GEHealthcare), 0.01% BSA). The γc surface was regenerated for cytokines IL-4 RQ and IL-4 RGA with 7 mM glycine (pH 3.0) and 250 mM NaCl. Kinetic data was determined using 120 s to 190 s of IL-4 variant association and 20 s to 900 s disassociation.

superkines exhibited substantially decreased binding to IL-13Rα1 ($K_D$=29,000 nM, and 21,000 nM, respectively). At physiological concentrations, these variants would exhibit negligible Type II receptor binding.

Thus, RGA has gained approximately 4-logs in binding affinity and is ~6-logs more selective for the Type-I receptor complex than to the Type-II receptor. Collectively, the structure-based and in vitro evolution approaches have yielded higher affinity and receptor-selective IL-4 variants for functional testing. These IL-4 muteins are referred to as IL-4 'superkines,' and specifically to the RGA variant as "super-4."

Example 3: Structural Basis of IL-4 Affinity Enhancement for γc

Ideally, the increased affinity of the IL-4 muteins, such as super-4, was realized with minimal disturbance of the wild-type IL-4/γc binding orientation. To determine if the super-4 docking mode with the second chain, γc, was perturbed relative to wild-type IL-4 crystallographic analysis was undertaken. Given the higher site 2 affinity of free (e.g., not bound to IL-4Rα) super4 for γc (KD~300 nM), it was

TABLE 1

Binding affinities of superkines for γc and IL-13Rα1.

| | Cytokine residue | | | | | | | | Affinity for γc | | | Affinity for IL-13Rα1 | | |
|---|---|---|---|---|---|---|---|---|---|---|---|---|---|---|
| | 117 | 118 | 121 | 122 | 124 | 125 | 128 | 129 | $K_d$ (nM) | $k_{on}$ (1/ms) | $k_{off}$ (1/s) | $K_d$ (nM) | $k_{on}$ (1/ms) | $k_{off}$ (1/s) |
| IL-4 | K | T | R | E | Y | S | S | S | 3300 | $9.5 \times 10^4$ | 0.31 | 4200 | $4.1 \times 10^4$ | 0.17 |
| RQ | | | Q | | | | | | 91 | $1.9 \times 10^5$ | $1.7 \times 10^{-2}$ | 29000 | — | — |
| RGA | R | V | Q | S | W | F | G | A | 0.89 | $6.6 \times 10^5$ | $5.9 \times 10^{-4}$ | 21000 | — | — |
| KF | | | | K | F | | | | 330 | $1.1 \times 10^5$ | $3.6 \times 10^{-2}$ | 250 | $7.3 \times 10^4$ | $1.8 \times 10^{-2}$ |
| KFR | | | | K | F | R | | | 6400 | $5.6 \times 10^4$ | 0.36 | 9.6 | $2.5 \times 10^5$ | $2.4 \times 10^{-3}$ |
| IL-13 | L | L | K | K | F | R | Q | F | U | | | 30 | | |

*U = unmeasureably weak

The $K_D$ of wild-type IL-4/IL-4Rα for IL-13Rα1, and γc were 4200 nM and 3300 nM, respectively. KF/IL-4Rα had greater affinity for binding to both IL-13Rα1 ($K_D$=250 nM), and γc ($K_D$=330 nM). The addition of the S125R mutation in KFR resulted in a 440-fold improvement in affinity for IL-13Rα1 ($K_D$=9.6 nM) but a decreased affinity for γc ($K_D$=6400 nM). Thus, KFR endowed IL-4 with a 2.6-log improvement in IL-13Rα1 binding affinity, and a corresponding 2-fold reduction in affinity for γc. The affinity enhancement was primarily due to a 3-log reduction in the off-rate. In this respect, the grafting was highly successful and resulted in a 3-log selectivity for IL-13Rα1 over γc. Parenthetically, the IL-4 D-helix library was also selected against IL-13Rα1, and this selection surprisingly resulted in a consensus sequence in which IL-4 residues 122, 124 and 125 were substituted with Lys, Phe, and Arg, respectively. This is nearly identical to the KFR engineered by grafting IL-13 residues on to wild-type IL-4 based on the structural overlap (FIG. 1b).

Figure 2:
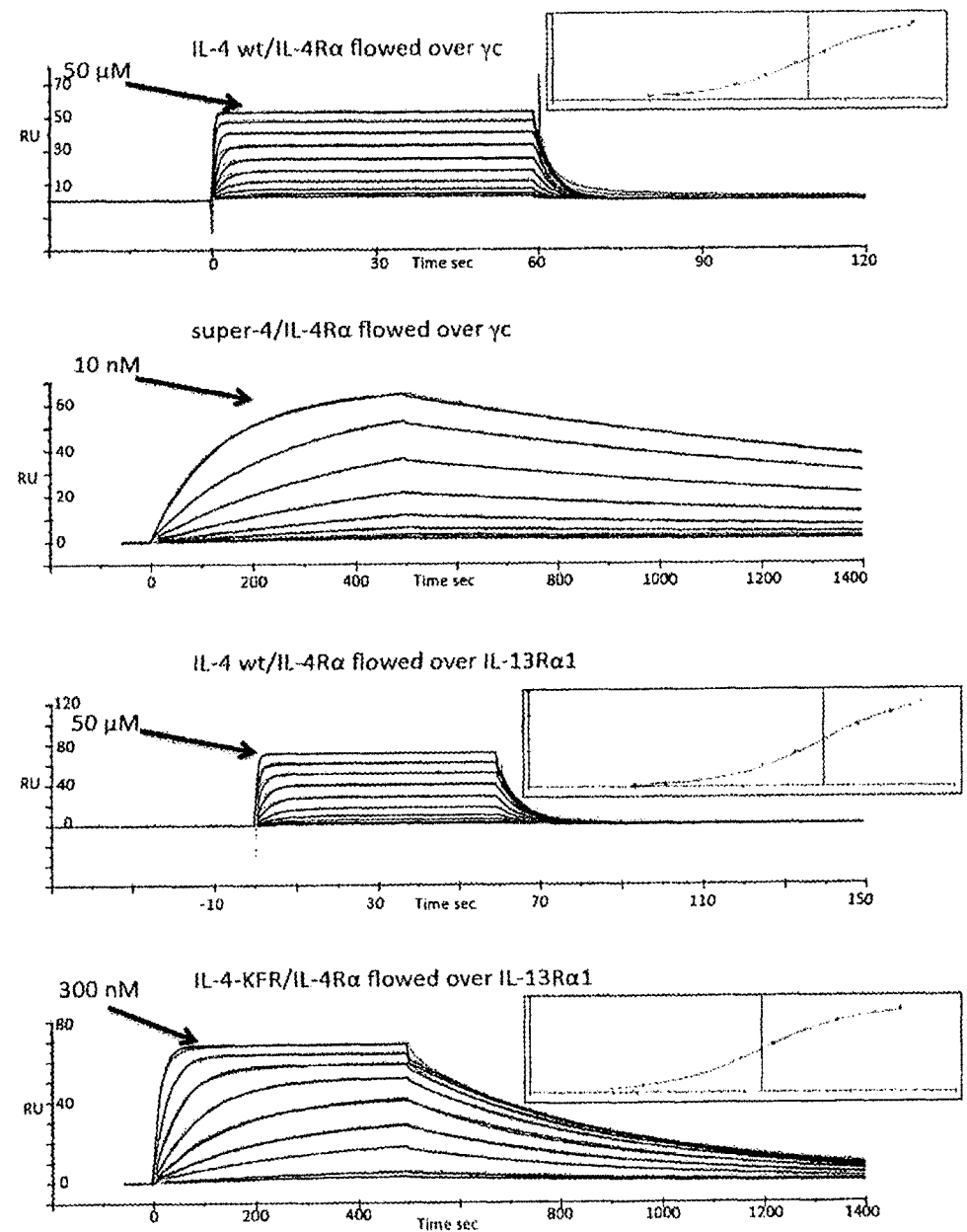
FIG. 2 depicts surface plasmon resonance analysis of IL-4 and synthekine binding to $γ_c$ immobilized on surface through C-terminal biotinylation.
Figure 3:
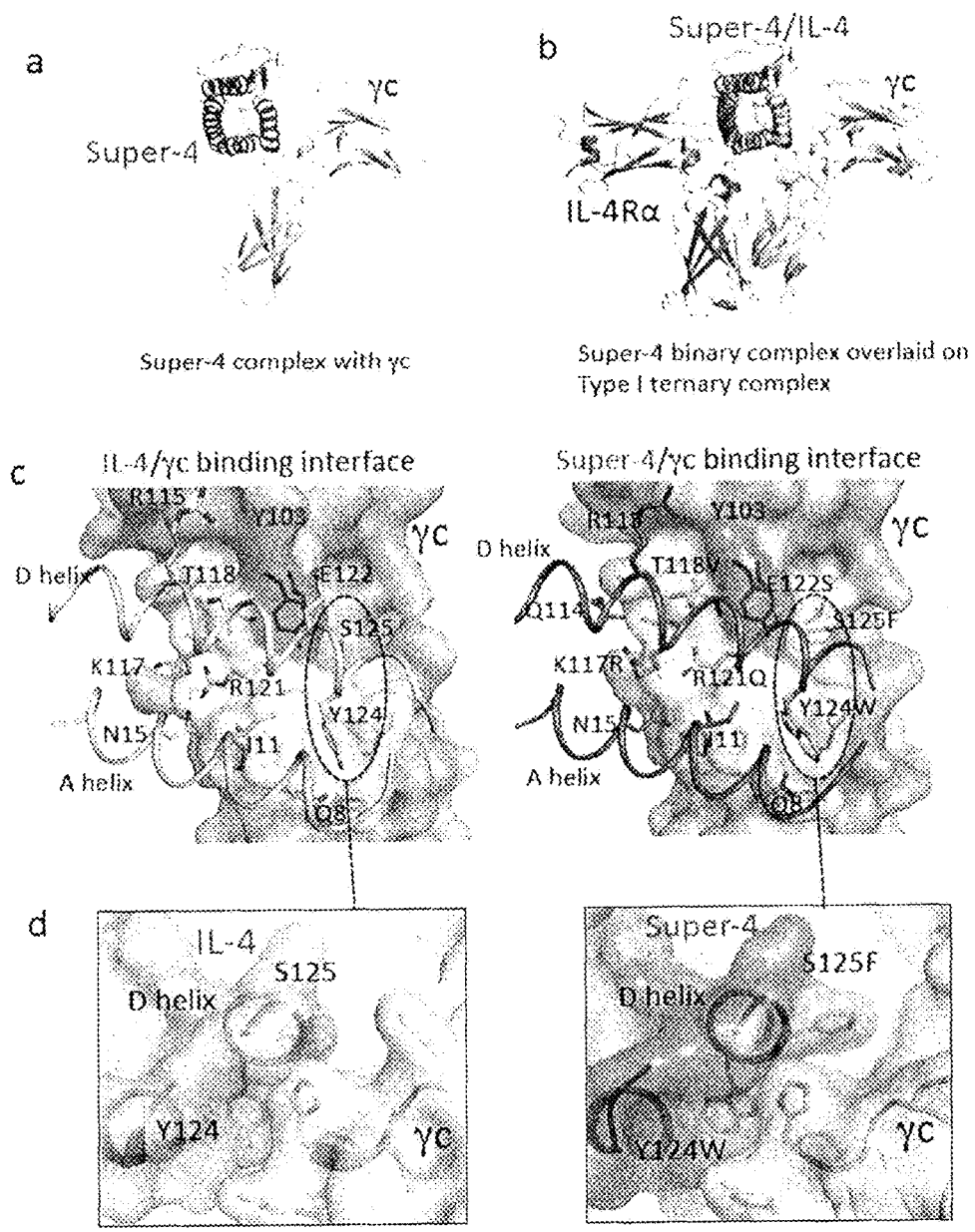
FIG. 3 depicts structural basis of IL-4 affinity enhancement for $γ_c$. (a) Crystal structure of the super-4/$γ_c$ binary complex at 3.25 Å. (b) Structural superposition of the super-4/γc binary complex with the IL-4/IL-4Ra/$γ_c$ ternary complex. The docking mode of super-4 with γc is essentially identical to that of IL-4. (d) Isolated view of the site 2 interfaces in the wild-type (left) and super-4 (right) complexes with $γ_c$. The view shown is the ribbon representation of the A and D helices of the cytokines, with $γ_c$-interacting side chains shown, projected onto the semi-transparent molecular surface of $γ_c$. The interacting residues of $γ_c$ underneath the surface are visible as dark outlines on the surface. The area contacted by the respective cytokines on $γ_c$ is indicated in yellow on the surface, and the energetically critical Y103 of $γ_c$ is colored red. A dashed oval encircles a region of the interface shown from the side in panel (d). In (d) a close-up is shown of the improvement in interface packing and shape complementarity in super-4 (right) versus IL-4 (left) by virtue of the S125F and Y124W substitutions in super-4. The semi-transparent molecular surfaces are shown for the cytokine and receptor.
Figure 4:
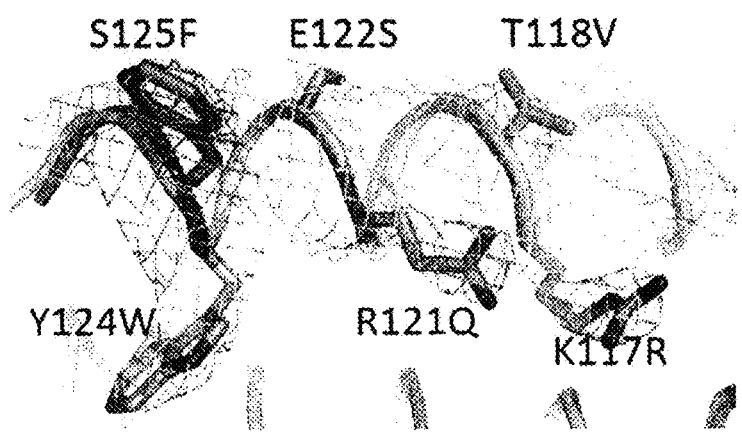
FIG. 4 depicts electron density of super-4 helix D.
Figure 5:
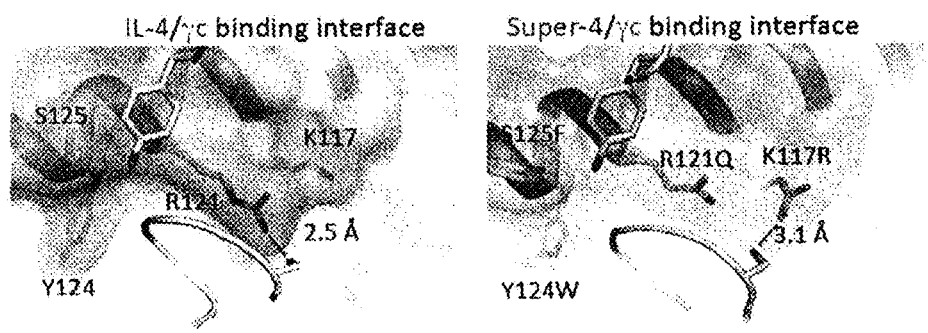
FIG. 5 depicts remodeled hydrogen bonding interactions in the super-4/γc interface.

When the RQ and RGA variants selected from yeast display were complexed with IL4Rα, exhibited substantially higher affinity binding to γc (Table 1, FIG. 2). RQ/IL-4Rα showed a 36-fold higher affinity for γc ($K_D$=91 nM) and RGA/IL-4Rα exhibited a 3700-fold higher affinity ($K_D$=0.89 nM) than did IL-4/IL-4Rα. The affinity increases of RQ and RGA were mainly due to reductions in off-rate, but also 7- and 6-fold faster on-rates. Both RQ and RGA possible to crystallize the binary super-4/γc complex in the absence of IL-4Rα to a resolution of 3.25 Å (FIGS. 3a and 4, Table 2).

TABLE 2

Data collection and refinement statistics (molecular replacement).

| | Super-4/γc |
|---|---|
| Data collection | |
| Space group | $P2_12_12_1$ |
| Cell dimensions | |
| a, b, c (Å) | 75.969, 105.879, 121.093 |
| α, β, γ (°) | 90, 90, 90 |
| Resolution (Å) | 50.00-3.25(3.37-3.25) |
| $R_{merge}$ | 16.1(99.0) |
| I/σI | 13.25(2.07) |
| Completeness (%) | 99.9(99.9) |
| Redundancy | 7.9 (7.9) |
| Refinement | |
| Resolution (Å) | 50.00-3.25 |
| No. reflections work/test | 15980/799 |
| $R_{work}/R_{free}$ | 23.1/29.2 |
| No. atoms | 5341 |
| Protein | 5341 |
| Ligand/ion | |
| Water | |

TABLE 2-continued

Data collection and refinement statistics (molecular replacement).

|  | Super-4/γc |
|---|---|
| B-factors | 95.1 |
| Protein | 95.1 |
| Ligand/ion | |
| Water | |
| R.m.s. deviations | |
| Bond lengths (Å) | 0.003 |
| Bond angles (°) | 1.324 |

To accomplish this IL-4 RGA/γc crystals were grown in sitting drops at 25° C. by mixing 0.1 µL protein [20 mg/mL in 10 mM HEPES-NaOH (pH 7.2) and 150 mM NaCl] with an equal volume of 50 mM HEPES (pH 7.2), 200 mM NaCl, and 30% PEG-4000. Crystals grew to a maximum size of 200×40×40 µM in 5-10 days. Crystals were flash frozen in liquid nitrogen using mother liquor containing 25% ethylene glycol as a cryoprotectant. A 3.3 Å data set was collected at beamline 8-2 at the Advanced Light Source. Diffraction data were processed using HKL2000.

The IL-4 RGA binary crystal structure was solved by molecular replacement with the program PHASER using the coordinates of IL-4 and γc separately (pdb code 3BPL). After the all domains were placed, the wild type sequence was converted to IL-4 RGA and iterative rounds of refinement with PHENIX and model adjustment with COOT were used to refine the structures. Ramachandran analysis was done using MolProbity (hypertext transfer protocol://molprobity.biochem.duke.edu). Buried surface area values were calculated using the Protein Interfaces, Surfaces, and Assemblies (PISA) server (hypertext transfer protocol://www.ebi.ac.uk/msd-srv/prot_int/pistart.html). IL-4 RGA consisted of 2 binary complexes. All structural figures and overlays were prepared using the PyMOL.

Superposition of the binary super-4/γc complex with the ternary Type-I signaling complex showed no major perturbations in cytokine-receptor orientation.

In the super-4/γc interface, side chain density was clear for super-4 helix D residues 117127 (FIG. 4); these engage the γc binding site in a topologically similar fashion to IL-4, with the γc hotspot residue Y124 occupying a central position (FIG. 2*c*). It appears that a possible mechanism underlying super-4's enhanced affinity was the replacement of S125 with F (FIG. 2*d*, left panel), which now inserts into a large hydrophobic pocket of γc that was previously unoccupied, contributing an additional 52.5 $Å^2$ of buried surface area (BSA) (FIG. 2*d*, right panel). The hydrophobic groove in γc occupied by IL-4 Y124 did not change in BSA when mutated to W in super-4, but this region of the contact interface gained a hydrogen bond from the Trp-N7 to a main chain carbonyl of γc. The R121Q superkine alone showed a substantial affinity increase by SPR (Table 2). This appears to be due to remodeled polar interactions (FIG. 5) in which a previous hydrogen bond between IL-4 R121 and γc S211 is lost, and replaced by the binding of K117R to 5211 of γc. A detailed comparison of amino acid interactions of IL-4 and super-4 with γc is presented in Table 3, which is a ligand-receptor contact table comparing interactions of γc with super-4 versus IL-4 (contacts represent van der Waals interactions unless indicated in bold type, which are within H-bonding distance).

TABLE 3

| Ligand-receptor contact table | | |
|---|---|---|
| γc | IL-4 wt | Super-4 |
| 45(VAL) | | 125(PHE) |
| 102(LEU) | 122(GLU) | 125(PHE) |
| 103(TYR) | 118(THR)<br>121(ARG)<br>122(GLU)<br>125(SER) | 115(ARG)<br>118(VAL)<br>121(GLN)<br>122(SER)<br>125(PHE) |
| 125(LYS) | 114(GLU)<br>118(THR) | 114(GLU) |
| 127(GLN) | 118(THR)<br>121(ARG) | 121(GLN) |
| 128(ASN) | 121(ARG) | |
| 159(HIS) | 124(TYR)<br>125(SER)<br>127(CYS)<br>128(SER) | 124(TRP)<br>125(PHE)<br>127(CYS) |
| 160(CYS) | 125(SER) | 125(PHE) |
| 182(TYR) | 8(GLN)<br>124(TYR) | 8(GLN)<br>124(TRP) |
| 207(PRO) | 11(ILE)<br>15(ASN)<br>121(ARG) | 11(ILE)<br>15(ASN)<br>121(GLN) |
| 208(LEU) | 8(GLN)<br>11(ILE)<br>12(LYS)<br>121(ARG)<br>124(TYR) | 8(GN)<br>11(ILE)<br>121(GLN)<br>124(TRP) |
| 209(CYS) | 121(ARG)<br>124(TYR)<br>125(SER) | 121(GLN)<br>124(TRP)<br>125(PHE) |
| 210(GLY) | 121(ARG) | 121(GLN) |
| 211(SER) | 121(ARG) | 15(ASN)<br>117(ARG)<br>121(GLN) |

Bold font in Table 3 represents potential H-bonds (3.5 Å cut off) or salt bridge from γc to Super-4. Italic font in Table 3 represents potential H-bonds (3.5 Å cut off) or salt bridge from γc to IL-4.

Example 4: IL-4 Muteins are Capable of Cell Activation

The affects of the disclosed IL-4 muteins on various cell types was tested. Since the equilibrium constants of the second chain recruitment of the superkines were dramatically different from that of IL-4, the behavior of the superkines in cell types that express mainly Type-I or Type-II IL-4-receptors or significant amounts of both were of tested.

At the outset RNA and protein expression of IL-4Rα, γc and IL-13Rα1 in several different human cell lines, including Ramos B-cells, HH T-cells, U937 monocytes and A549 epithelial cells was determined. Ramos, U937, A549 and HH cells were grown in RPMI containing 10% FBS, penicillin/streptomycin and I-glutamine (2 mM) and maintained at 37° C. with 5% $CO_2$. Cells were serum starved overnight and harvested. RNA was isolated from starved cells with RNeasy® Kit (Qiagen). RNA was reverse-transcribed to cDNA using SuperScript® II First-Strand Synthesis System for RT-PCR (Invitrogen). Quantitative PCR reactions were performed using a 7900HT sequence detection system (Applied Biosystems). The primer/probe sets to detect IL-4Rα, IL13Rα1 and γc (FAM-MGB probe), and TaqMan Ribosomal RNA Control Reagents for detecting the 18S (VIC-MGB probe) ere from Applied Biosystems. The mRNA levels were normalized to 18S ribosomal RNA. The relative expression of mRNA of each receptor chain by real-time PCR is depicted in FIG. 3a. Ramos cells had ~3-4 times more IL-4RαmRNA than the other cell lines. The HH T-cell line and the U937 monocyte line had abundant expression of the γc whereas Ramos expressed low but measurable levels of γc. A549 had low or undetectable amounts of γc. For IL-13Rα1, the A549 epithelial cell line had the highest expression and U937 cells had clearly detectable amounts of the receptor, whereas in Ramos and HH cells, mRNA expression of the IL-13Rα1 was at the lower limit of the sensitivity of the PCR.

Thus, based on mRNA levels, Ramos cells have relatively little Type-II IL-4 receptor. Although they have large amounts of IL-4Rα, their amounts of the Type-I receptor are limited by relatively low expression of γc. A549 cells have abundant Type-II receptor and little or no Type-I receptor. Finally, U937 cells have substantial amounts of both Type-I and Type-II receptor chain RNA.

Figure 6:
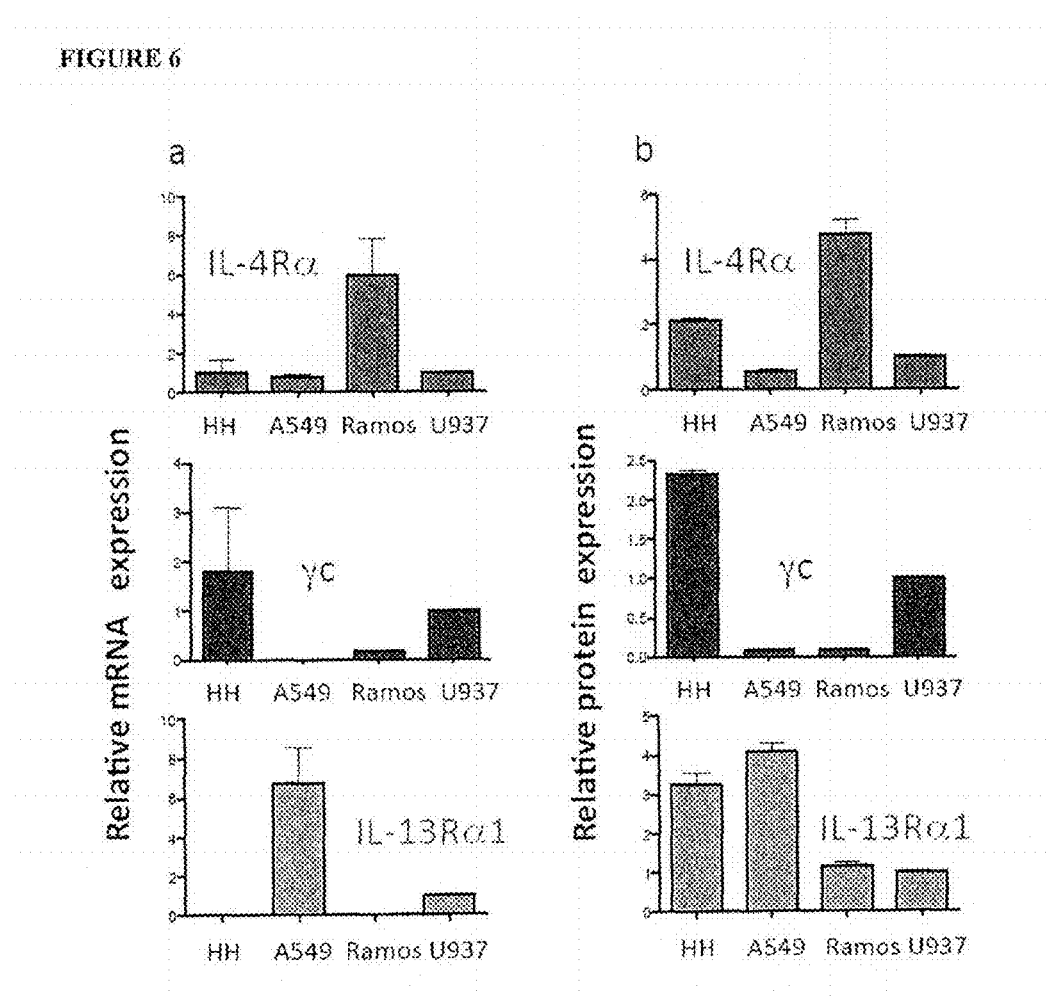
FIG. 6 depicts expression of IL-4 receptor components on cell lines. (a) Expression of mRNA for IL-4Rα, γc and IL-13Rα1 was measured by quantitative PCR as described in materials and methods on cells that had been starved overnight. Results represent means and SEMs from three independent experiments. (b) Expression of IL-4Rα, γc and IL-13Rα1 on cell surface of indicated cell lines was determined by flow cytometry. The MFI measured with specific antibody was normalized to a control antibody of the same isotype.

By FACS staining, Ramos showed high expression of IL-4Rα. HH and U937 had highest expression of γc, whereas Ramos showed relatively low expression of this chain. IL13Rα1 expression was highest in A549 cells (FIG. 6b). Cell surface expression of IL-4 receptor chains was performed after blocking Fc receptors I, II and III. Antibodies to CD23, IL-4Rα and γc antibodies were purchased from BD and for IL-13Rα1 from R&D.

Determination of STAT6 Y641 phosphorylation provided a quantitative tool to measure a very early event in IL-4 signaling that directly depended upon assembly of a receptor complex competent to transduce an intracellular signal. STAT6 Y641 phosphorylation requires activation of the Jak kinases and the phosphorylation of intracellular tyrosines of IL-4Rα, particularly Y575, Y603, and Y631. These phosphorylated tyrosines serve as docking sites for the SH2 domain of STAT6, which then becomes phosphorylated at Y641, resulting in STAT6 dimerization and subsequent entry into the nucleus.

To study responses to IL-4 and its superkines, the cell types described above were used. The stimulatory activity of IL-4, the super-4 and KFR superkines were tested. Super-4, when complexed to IL-4Rα, has the highest KD for binding to γc and KFR has the highest KD for binding to IL-13Rα1.

Figure 7:
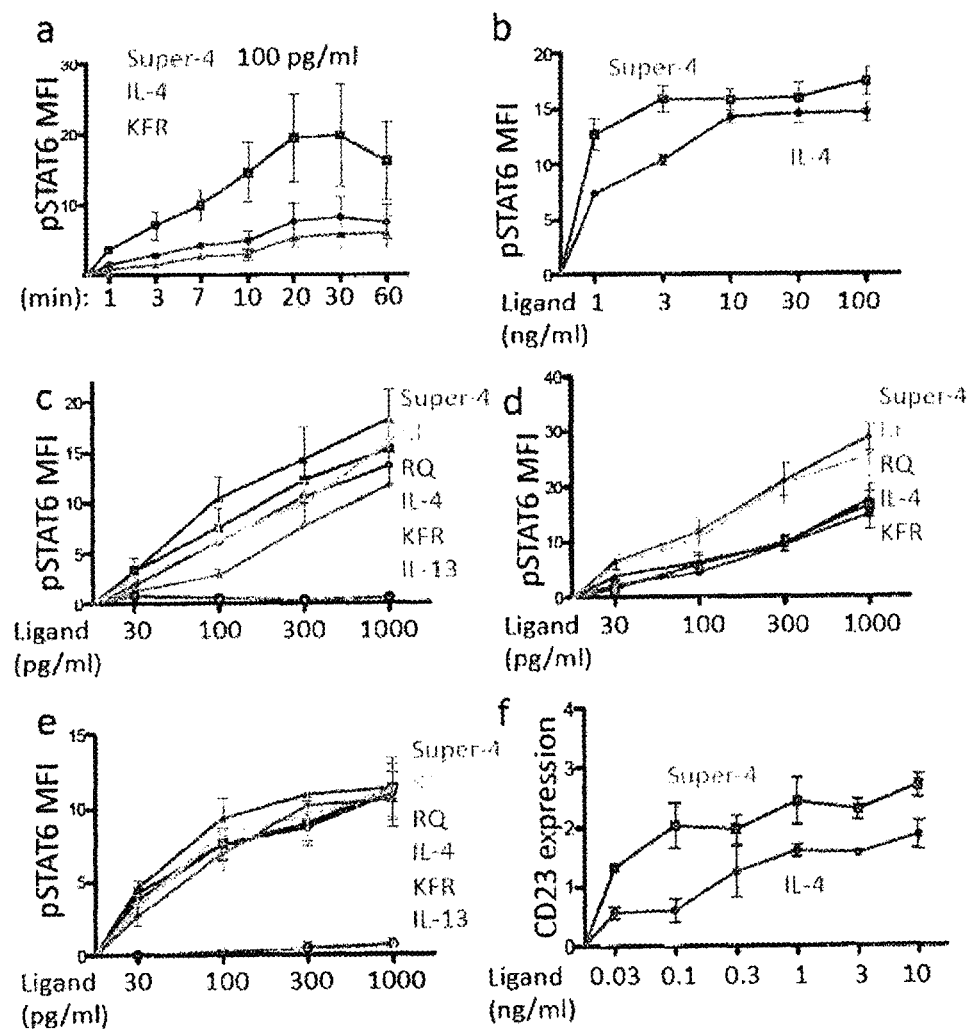
FIG. 7 depicts the effect of IL-4 superkines on intracellular signaling. (a) Overnight starved Ramos cells were unstimulated or stimulated for indicated times with 100 pg/ml of IL-4, super-4 or KFR. The cells were then fixed, permeabilized and stained with antibody against phosphorylated STAT6. Three independent experiments were performed with means and SEMs indicated. (b) Ramos cells were stimulated for 15 minutes with increasing amounts of IL-4 or super-4, the analysis was then performed as in FIG. 7(a). The experiment was repeated three times; means and SEMs are indicated. (c) Ramos cells were starved overnight, followed by stimulation with increasing amounts of IL-4 or the indicated superkines for 15 minutes. Means and ±SEMs of three independent experiments are indicated. (d) A549 cells were starved overnight, stimulated with indicated concentrations of IL-4 or superkine for 15 minutes. Cells were fixed and prepared as in 7(a); three independent experiments were performed and means and SEMs are indicated. (e) U937 cells were starved overnight, followed by 15 minutes stimulation with IL-4 or a superkine; pSTAT6 was measured as in 7(a). The experiment was repeated three times; means and SEMS are indicated. (f) Ramos cells were stimulated for 8 hours either with IL-4 or super-4 as indicated, followed by surface staining of CD23. The experiment was repeated three times; the means and SEMs of upregulation of CD23 are indicated.
Figure 8:
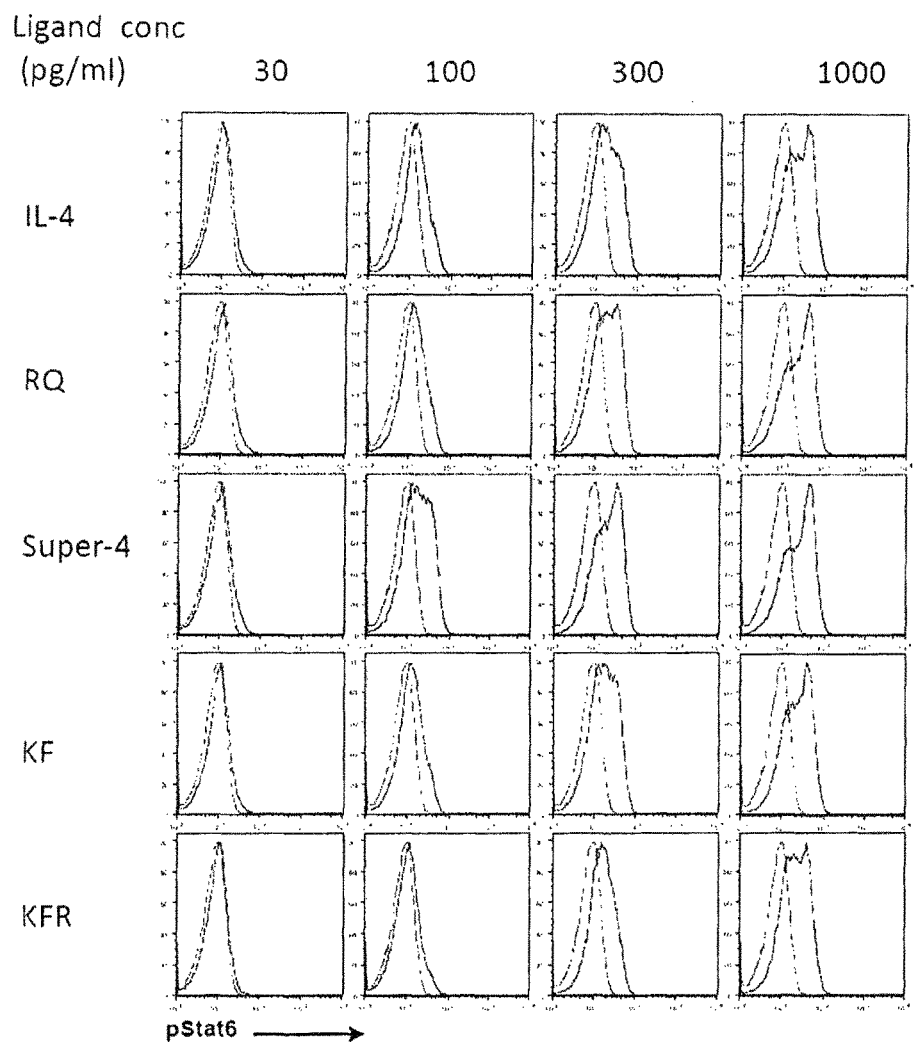
FIG. 8 depicts STAT6 phosphorylation staining in response to IL-4 and superkines from a single experiment.

Ramos cells were used to study IL-4 responses dominated by the Type-I receptor complex (FIGS. 7 and 8). Stimulating Ramos cells with 100 pg/ml (~7 pM) of either IL-4 or the super-4 or KFR superkines for various times, it was found that maximal induction at 20 minutes of stimulation that persisted at 30 minutes and then slightly diminished at 60 minutes (FIG. 4a). The time course of stimulation of STAT6 phosphorylation by IL-4, super-4 and KFR is similar, but super-4 induces substantially more phosphorylation than does IL-4 or KFR at all time points measured; after 20 minute stimulation, the mean MFI of STAT6 phosphorylation induced by super-4 is 19.6, by IL-4, 7.7 and by KFR, 5.4.

Prior to stimulation, cells were cultured overnight in growth medium containing 2% FBS ("starved"). Intracellular pSTAT6 staining was performed after ice-cold methanol (90%) permeabilization. Anti-pSTAT6 antibody was purchased from BD Biosciences. The induction of STAT6 phosphorylation was calculated by subtracting the Mean Fluorescence Intensity (MFI) of the stimulated sample from unstimulated sample.

The concentration/response curves for IL-4, super-4, KFR as well as RQ and KF were determined as well. Starved Ramos cells were stimulated for 15 minutes with concentrations of IL-4 or of the superkines ranging from 30 pg/ml (2 pM) to 100,000 pg/ml (7.4 nM), although in most experiments the range was limited to 30 to 1,000 pg/ml. IL-4 and super-4 both caused similar amounts of STAT6 phosphorylation but super-4 required 1,000 pg/ml to reach plateau levels whereas IL-4 required between 10,000 and 30,000 pg/ml to achieve plateau levels (FIG. 7b).

An analysis of the response of Ramos cells to IL-4 and the four superkines in the concentration range of 30 to 1000 pg/ml was carried out (FIGS. 7c and 8). Super-4 was superior to IL-4 at all concentrations tested; ~3-fold more IL-4 is required to achieve the same degree of STAT6 phosphorylation as was achieved by super-4. KF, RQ and IL4 were generally similar to one another; KFR caused less stimulation than IL-4, being somewhat less than 3-fold less active. As a consequence, super-4 is ~10-fold more active than KFR. Thus, qualitatively, the superkine-IL-4 that forms an IL-4/IL-4Rα complex with the highest affinity for γc is the most active in Ramos cells and the superkine with the lowest affinity is the least active. However, the relative advantage of super-4 over IL4 was relatively modest in comparison with the ~3700-fold difference in their solution equilibrium constants for γc when complexed to IL-4Rα.

A similar analysis was carried out on A549 cells that, as noted above, principally utilize IL-13Rα1 as their second chain. For these cells, KFR and KF were 3-10-fold more stimulatory than IL-4; super-4 and RQ were indistinguishable from IL-4 (FIG. 4d). While KFR, complexed to IL-4Rα, had a ~400-fold greater affinity in solution for IL-13Rα1 than did IL-4, KF had only an ~10-fold advantage over IL-4. Still, there was a qualitative agreement in that higher affinity superkines caused better responses but their degree of advantage was not directly correlated with their solution affinity difference.

Example 5: Modeling of the Receptor Assemblage

The notion that super-4 was a ~3-10 more potent activator of STAT6 phosphorylation while the three dimensional equilibrium for γc was ~3700 higher than that of IL-4 spurred an analysis of how signal-inducing receptor formation is dictated by the expression of the second chain. It had been calculated that in macrophages ~40 receptors would give nearly maximal STAT6 activation. Therefore the surprisingly modest advantage super-4 had at the cellular level might have to do with the relative low number of formed receptor complexes and/or could only be observed as when the number of second chains is low, e.g. the ligand will compete on available second chains.

To address this question a computational approach was utilized. A Matlab® script that predicts assemblage of receptor complexes as a function of ligand concentration upon varying second chain numbers and varying second chain equilibrium constant values was applied.

Figure 9:
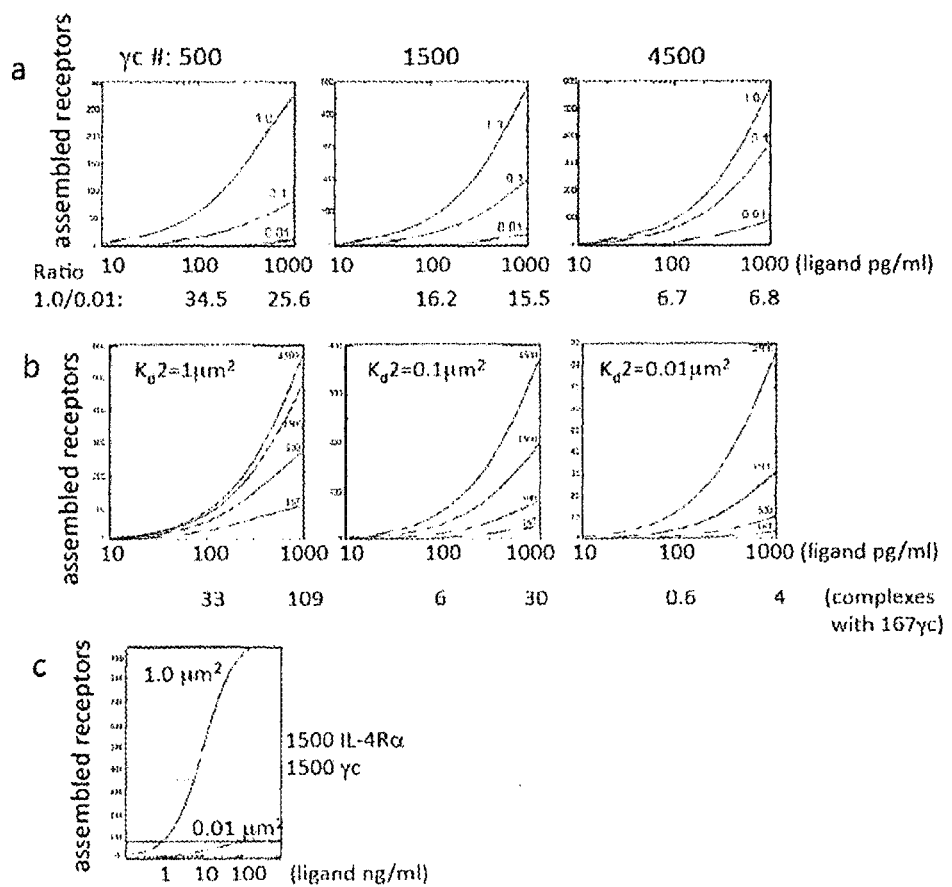
FIG. 9 depicts modeling of receptor assemblage in response to enhancement of second chain recruitment and varying number of second chains. The Matlab script was used to calculate assemblage of IL-4 receptors on cell surfaces expressing only the type I IL-4 receptor. (a) In the top three panels, IL-4Rα number was set to 1500. Second chain number was raised from 500 to 4500 and 2-dimensional equilibrium constant of IL-4Rα complexes for second chain were over a range from 0.01 μm² to 1 μm² as indicated. The ratio of assembled chains of highest (1.0 μm²) versus lowest (0.01 μm²) second chain K values was calculated for 100 and 1000 pg/ml at 500, 1500 and 4500 γc molecules per cell. (b) In the middle three panels, IL-4Rα number was set to 1500. 2-D equilibrium constant was varied from 1 μm² to 0.01 μm² and second chain number from 167 to 4500 per cell. Complexes assembled with 167 γc chains per cell at 100 and 1000 pg/ml of IL-4 or muteins at 2-D equilibrium constants of 1.0 μm², 0.1 μm² or 0.01 μm² are shown. In the bottom panel, number of assembled complexes is plotted against IL-4 or super-4 concentration and a line is drawn to the maximum number of assembled receptors for IL-4 in the 10,000 to 30,000 pg/ml concentration range.

Since the number of IL-4Rα chains on Ramos cells is 1500, the assemblage of receptors was fixed to this number. A relatively modest effect was calculated for increasing second chain K from 0.01 to 1.0 when γc number was set to 4500 but when γc chain number was set to 500, the increase in second chain K had a strong impact on the number of receptor chains assembled (FIG. 9a compare left and right panels).

Thus, with a cytokine concentration of 100 pg/ml, the ratio of assembled complexes for K=1 µm$^2$ compared to K=0.01 µm$^2$ was 6.7 when the number of second chains was 4500 while that ratio was 34.5 when the γc number was set to 500. When cytokine concentration was ten-fold higher, 1000 pg/ml, the K=1 µm$^2$/K=0.01 µm$^2$ ratio for 4500 γc molecules was 6.8 while it was 25.6 when the γc number was 500. Thus, increasing secondary chain K becomes more useful when the secondary chain number is relatively low. This would effectively mean that a cell that expresses low levels of γc or of IL-13Rα1 would most strongly benefit from enhanced affinity for the second chain but that cells that express large numbers of γc or IL-13Rα1 should discriminate less well between high affinity superkines and IL-4.

An alternative question would be the effect of increasing affinity of the superkine/IL-4Rα complex on the assemblage of complexes on cells that have very few γc molecules per cell. The assemblage of receptor complexes was calculated when the 2-dimensional K was held constant and the number of γc molecules varied from 4500 to 167. At the concentration of cytokine used for most of the stimulation assays in vitro, an IL4/IL-4Rα complex that had a 2-dimensional K for γc of 0.01 µm$^2$, which is the suggested 2 dimensional K for IL-4, assembled very few receptors on cells that had only 167 γc molecules (<1 at 100 pg/ml and 3.6 at 1000 pg/ml) (FIG. 9b, right panel). Thus, such cells should be essentially unresponsive to IL-4 at these cytokine concentrations. By contrast, a superkine that would have a 2-dimensional K for γc of 1 µm would assemble 33 complexes at 100 pg/ml and 109 complexes at 1000 pg/ml (FIG. 9b, left panel).

In order to assess how many assembled complexes are theoretically sufficient for maximal stimulation in Ramos cells, it was determined whether IL-4 and RGA stimulate similar plateau values for STAT6 phosphorylation. Indeed, they did; the plateau is achieved at between 10,000 and 30,000 pg/ml of IL-4 in Ramos cells (FIG. 7b). The number of assembled complexes for a ligand that had low affinity for the second chain (0.01 µm) was calculated using an intermediate number of γc chains (1500) at 10,000 and 30,000 pg/ml. The value for assembled chains was between 65 and 71 (FIG. 9c), implying that assembling more chains may not lead to any greater signaling. If a low γc number (500) was chosen, the number of assembled chains for maximal stimulation would have been correspondingly lower. However, a value of ~70 assembled receptors giving a maximal signal is a conservative estimate.

Thus, the 33 assembled complexes achieved by the high affinity superkine used at 100 pg/ml should be sufficient for a substantial response by cells expressing 167 γc molecules and the 109 complexes assembled at 1000 pg/ml should have yielded a maximal response. This implies that cells that would not have responded to IL-4 at these low concentrations would respond to the high affinity superkine, raising the possibility that unanticipated responses (and toxicities) might be achieved by engineering IL-4 superkines with very high affinity for the second chain.

Example 6: Altering Second Chain Expression

Figure 10:
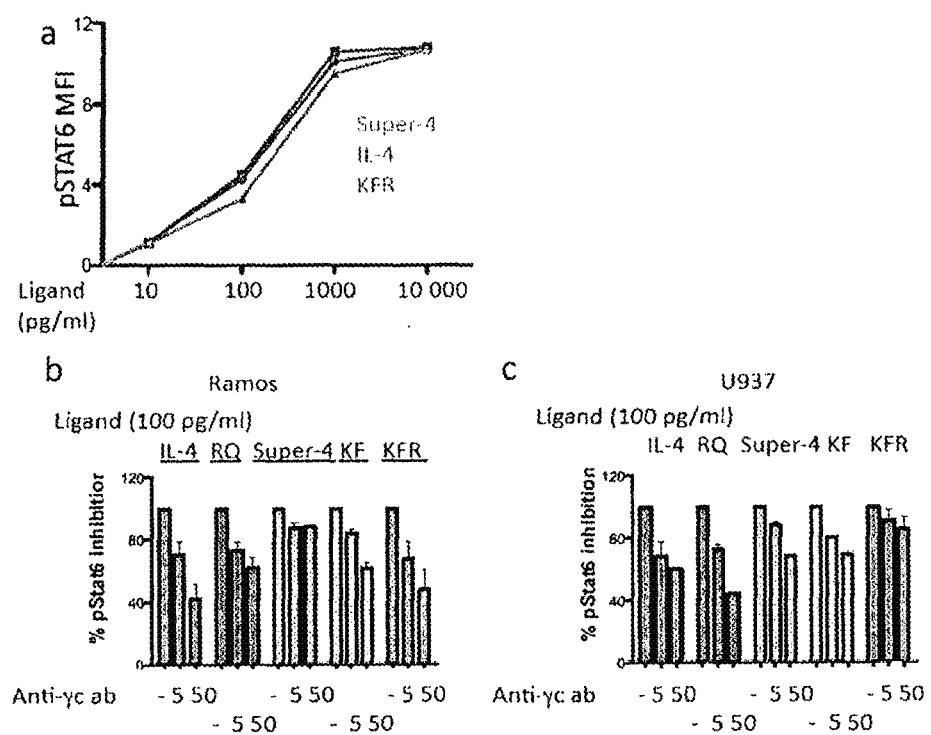
FIG. 10 depicts the effect of altering γc availability on IL-4- or superkine-induced STAT6 activation. (a) HH-cells were stimulated with indicated concentrations of IL-4 or muteins, the intracellular staining and analysis was performed as in FIG. 7. Representative experiment of two independent experiments with identical results is shown. (b) Starved Ramos cells were either left untreated, or incubated for 1 hour with 5 or 50 μg/ml of anti-γc blocking antibody. The cells were then stimulated with 100 pg/ml of IL-4 or indicated superkine. The analysis was then performed as in FIG. 7a. Three independent experiments were performed, means and SEMs are indicated. (c) Starved U937 cells were treated and analyzed as Ramos cells in 10b.

Because an increase in γc expression could be expected to decrease the advantage super-4 had over IL-4, the sensitivity to IL-4 and super-4 was studied in the HH cell line that had much higher expression of γc than Ramos cells (FIGS. 6a and b). Super-4 was not superior to IL-4 in inducing phosphorylation of STAT6 in HH cells over a concentration range of 10 pg/ml to 10,000 pg/ml (FIG. 10a).

Figure 18:
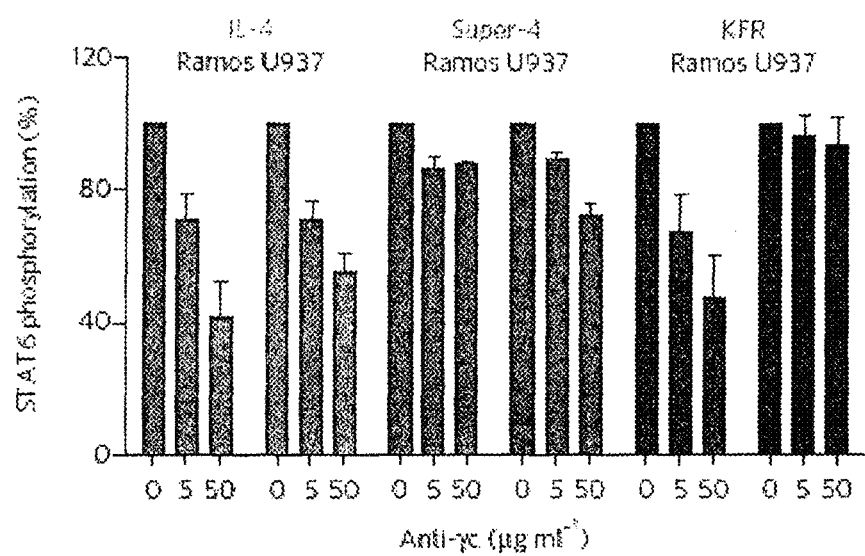
FIG. 18 illustrates phosphorylation of STAT6 in Ramos and U937 cells in response to IL-4, super-4, and KFR in the presence of anti-γc (0 μg/ml, 5 μg/ml, or 50 μg/ml). Response in the absence of anti-γc was normalized to 100%, and responses in the presence of anti-γc are expressed in relation to the normalized value. Data (mean±s.e.m.) are from three independent experiments.

An alternative test of the contribution of secondary chain number on relative responses to IL-4 and the superkines would be to diminish the accessibility of γc. For this purpose, varying concentrations of anti-γc antibody were added to the stimulation culture. Stimulating Ramos cells with 100 pg/ml of super-4 resulted in substantial advantage over 100 pg/ml of IL-4 as judged by STAT6 activation (FIG. 7c). These cells were stimulated with 100 pg/ml of IL-4 or the super-4/RQ/KF/KFR superkines in the presence or absence of anti-γc, measured the phosphorylation of STAT6 by flow cytometry and calculated the percentage decrease in STAT6 phosphorylation caused by anti-γc. STAT6 phosphorylation induced by IL-4 was decreased 58% by 50 µg/ml of anti-γc whereas for super-4, the decrease was only 12% (FIG. 10b; FIG. 18). For the RQ and KF superkines, the inhibition was ~40% and for KFR, the inhibition was similar to that for IL-4. These results are consistent with the relative solution KD's of IL-4 and the superkines for binding to γc (super-4>RQ,KF>IL-4=KFR, Table 1) and support the concept that increased affinity for the second chain results in greater stimulatory discrimination when the second chain expression is diminished.

Similar γc blocking experiments were performed on the U937 monocyte cell line. For γc blocking experiments, overnight starved Ramos or U937 cells were incubated for 1 hour at 37° C. with blocking antibody.

The U937 cell line expresses both Type-I and Type-II IL-4 receptors and blocking of γc could be expected to diminish IL-4 responses, whereas there should be little impact on the activity of the KFR superkine because of its principle utilization of the type II receptor. Indeed, blocking γc in U937 cells resulted in 44% reduction in STAT6 phosphorylation in response to IL-4 but only a 7% reduction in response to the KFR superkine (FIG. 10c).

Example 7: Primary Human Cell Responses to IL-4 and Superkines

Figure 11:
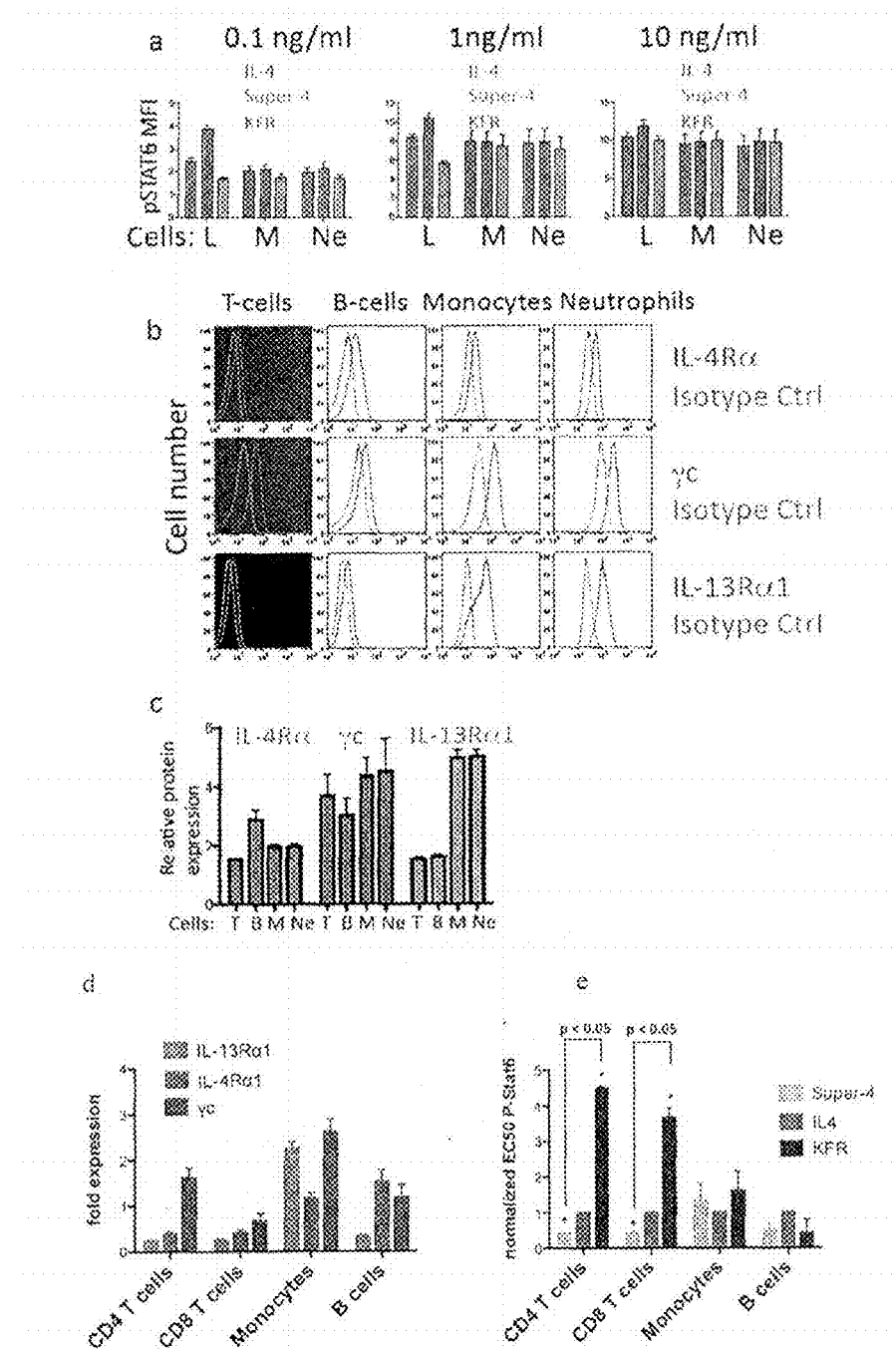
FIG. 11 depicts the behavior of superkines on human primary cells. (a) PBLs stimulated for 15 minutes with indicated concentrations of IL-4, super-4 or KFR or left unstimulated. The induction of pSTAT6 was calculated as in FIG. 7; means and SEMs of data from 5 donors are indicated. (L=lymphocytes, M=monocytes, Ne=neutrophils) (b) Expression of IL-4 receptor chains on human PBLs from a single donor was measured as in FIG. 6b. For the measurement of IL-4Rα, γc and IL-13Rα1 expression, B- and T-cells were gated by cell surface markers (CD19, CD3), while monocytes and neutrophils were identified as CD19 and CD3 negative cells, based on their distinctive forward and side scatters. Appropriate isotype controls served as negative control. (c) IL-4R receptor chain expression on PBLs from six donors was measured as in FIG. 11b; means and SEMs are presented (T=T-cell, B=B-cell, M=monocyte, Ne=neutrophil). (d) Expression of IL-4 Type-I and Type-II receptor chains on human PBLs. For the measurement of IL-4Rα, γc and IL-13Rα1 expression, B and T cells were gated by cell surface markers (CD19, CD4, CD8), while monocytes were identified as CD14+ cells. Appropriate isotype controls served as negative control, means and SD are presented. (h) Normalized pSTAT6 EC50 values obtained based on sigmoidal dose response curves of IL-4 and the superkines (FIG. 19). pSTAT6 EC50 values from IL-4 wt were normalized to 1 and the EC50 values of the super-4 and KFR were calculated accordingly. Paired T-test was used to determine significant changes.

To confirm that the responses to the various superkines depended on which secondary chain they primarily used, Stat6 phosphorylation responses of human peripheral blood leukocytes (PBL) was tested (FIG. 11). PBLs were either unstimulated or stimulated with IL-4 or the various superkines for 15 minutes. STAT6 Y641 phosphorylation was measured by flow cytometry to test the responsiveness of various peripheral blood cell types. The lymphocyte response to super-4 was significantly better at low ligand concentrations.

The P value for the comparison of advantage of STAT6 phosphorylation by super-4 over IL-4 at 100 pg/ml was 0.0003, at 1 ng/ml the P value was 0.0104 and at 10 ng/ml P value was not statistically significant (0.1493). In comparison, the corresponding P values for comparing the advantage of IL-4 over KFR-superkine in lymphocyte STAT6 phosphorylation were 0.0005, 0.0004 and 0.5364. These findings are consistent with the primary use of γc as the second receptor chains in human lymphocytes (FIG. 11a). Monocytes and neutrophils showed little difference in their responses to IL-4, super-4 and KFR.

To confirm the degree of expression of Type-I and Type-II IL-4 receptor on primary cells, IL-4Rα, γc and IL-13Rα1 in B-cells, T-cells, monocytes and neutrophils from 6 healthy donors was measured by flow cytometry. IL-4Rα expression was highest on B-cells while monocytes and neutrophils showed little difference in IL-4Rα expression and T cells had the least IL-4Rα(FIGS. 11b, 11c, and 11d). For γc, there was relatively little difference in expression between monocytes and CD4 T cells. B cells had slightly less γc and CD8 T cells had the lowest levels. As expected, IL-13Rα1 expression was highest on monocytes, whereas B and T cells showed very low expression of this chain. PBLs were either unstimulated or stimulated with IL-4 or the various superkines for 15 minutes; STAT6 Y641 phosphorylation was measured by flow cytometry. Super-4 induced stronger phosphorylation of STAT6 than IL-4 and much stronger phosphorylation than KFR in CD4 and CD8 T cells (FIG. 11e). Monocytes showed little difference in their responses to IL-4, super-4 and KFR, in keeping with their expression of both γc and IL-13Rα1.

Figure 12:
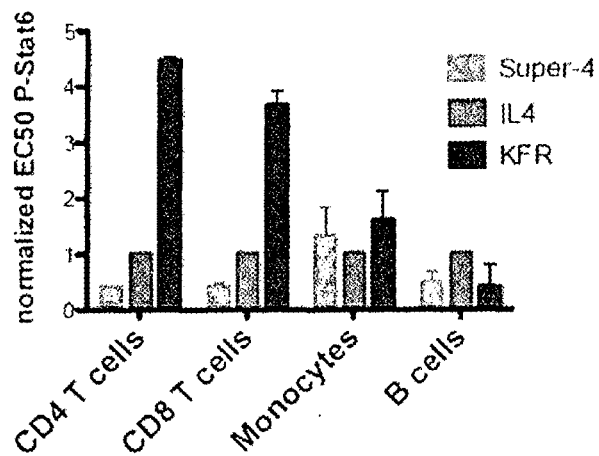
FIG. 12 depicts that super-4 induced stronger phosphorylation of STAT6 than IL-4 and KFR in CD4 and CD8 T cells. Normalized P-STAT6 EC50 values obtained based on sigmoidal dose-response curves of IL-4 and the superkines. P-STAT6 EC50 values from IL-4 wild-type were normalized to 1 and the EC50 values of the super-4 and KFR were calculated accordingly (L=Lymphocytes, M=monocyte, Ne=neutrophil).

Super-4 induced stronger phosphorylation of STAT6 than IL-4 and substantially stronger phosphorylation than KFR in CD4 and CD8 T-cells (FIG. 12). Monocytes showed little difference in their responses to IL-4, super-4 and KFR. Somewhat surprisingly, B cells responded well to KFR despite their relatively low level of detectable IL-13Rα1.

$T_H9$ Differentiation Assay

To study the functional specificity and immunomodulatory abilities of IL-4 and the superkines, a series of experiments involving CD4 T-cells and monocytes was performed. The combination of TGF-β and IL-4 promotes the differentiation of naïve human CD4 T cells into $T_H9$ cells. To test whether super-4 more potently induces $T_H9$ differentiation than wild-type IL-4, naïve CD4$^+$CD45RA$^+$CD45RO$^-$CD25$^-$ T-cells were isolated.

Enriched CD4$^+$ T cells were prepared from buffy coats obtained from healthy donors (Stanford Blood Center) using RosetteSep™ Human CD4$^+$ T Cell Enrichment (Stem Cell Technologies) prior to density gradient centrifugation with Ficoll-Paque™ PLUS (GE Healthcare). Naïve CD4$^+$CD45RA$^+$CD45RO$^-$CD25$^-$ T cells were magnetically sorted with Naïve CD4$^+$ T Cell Isolation Kit II (Miltenyi Biotec).

Cells were then cultured at 37° C. in 48-well flat-bottomed plates (Falcon) in X-VIVO™ 15 media (Lonza) supplemented with 10% Human Serum Type AB (Lonza), 100 units/ml penicillin/streptomycin, L-glutamine (Invitrogen) and 50 μM β-mercaptoethanol (Sigma-Aldrich). Cells were cultured at 2.5×105 cells/mL with anti-CD3/CD28 coated beads (Invitrogen) at a 1:1 bead-to-cell ratio in the presence of 5 ng/mL TGF-β (eBioscience) and the indicated concentrations of IL-4, super-4 or KFR.

After 4 days in culture, beads were magnetically removed and cells were restimulated with 25 ng/mL PMA and 750 ng/mL Ionomycin (Invitrogen) in the presence of Brefeldin A (eBioscience) for 4 hours. Cells were then stained with a LIVE/DEAD® Fixable Aqua Dead Cell Stain Kit (Invitrogen), then fixed and permeablized (eBioscience) according to manufacturer's protocols. Subsequently, cells were stained with fluorescently labeled Abs against IL-9 and Foxp3 (eBioscience). Labeled cells were analyzed on a BD LSRII (BD Bioscience), and FACS plots were further analyzed by FlowJo (Treestar). All FACS data shown are gated on singlets and live cells.

Figure 13:
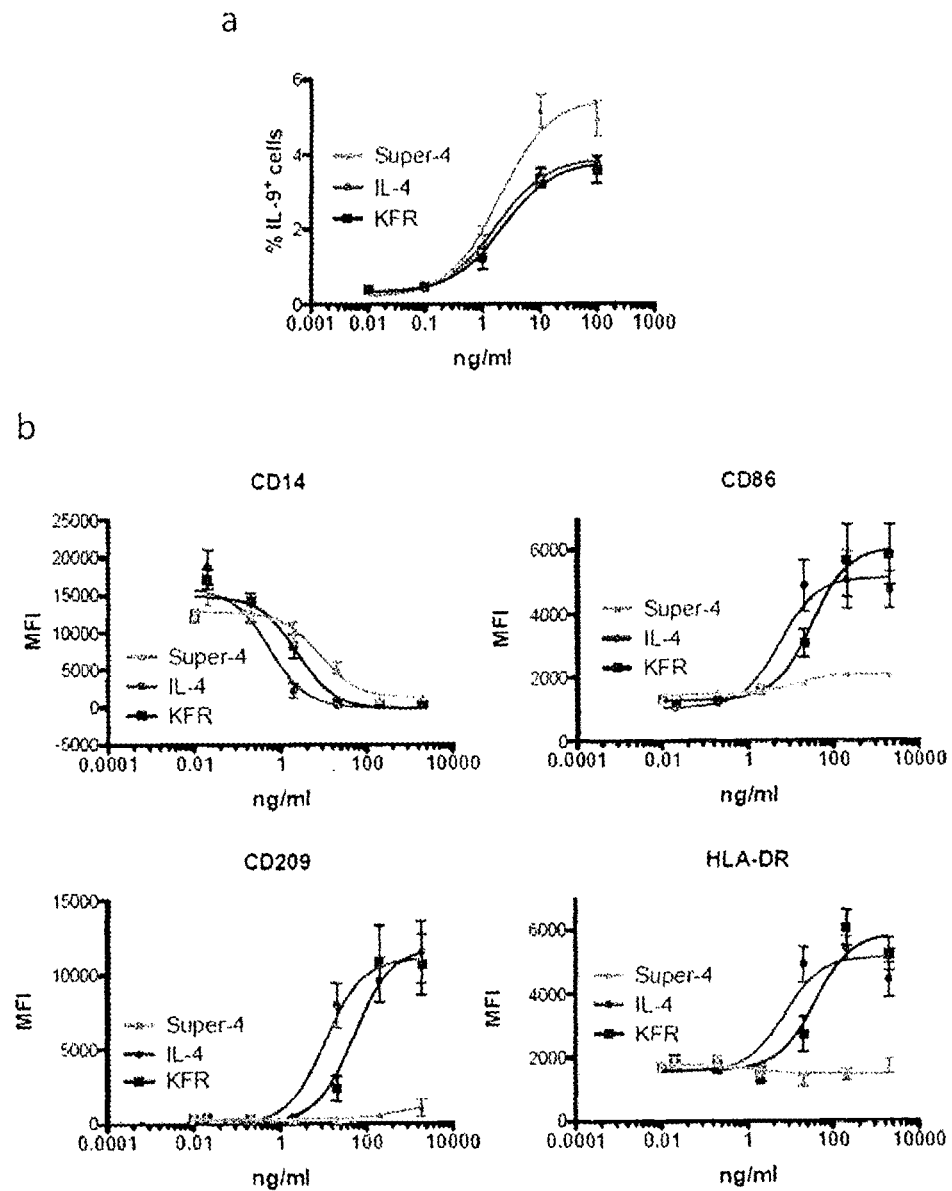
FIG. 13 depicts the functional activities exhibited by IL-4 and superkines. (a) Human naïve CD4⁺CD45RA⁺CD45RO⁻CD25⁻ T cells were cultured with anti-CD3/anti-CD28-coated beads in the presence of TGF- and the indicated concentrations of IL-4, super-4, or KFR. After 4 days, cells were restimulated with PMA and ionomycin in the presence of Brefeldin A for an additional 4 hours. Cells were subsequently analyzed for intracellular expression of IL-9 and Foxp3. Data (mean and SEM) are from 3 independent experiments with >4 donors. (b) CD14$^+$ monocytes were isolated (>97% purity) from peripheral blood mononuclear cells obtained from healthy blood donors and cultured with 50 ng/mL GM-CSF alone or with the indicated concentrations of IL-4, KFR or super-4.

Priming with 10 or with 100 μg/ml of super-4 resulted in a significantly higher percentage of cells that produced IL-9 upon subsequent stimulation with PMA and ionomycin than did priming with the same concentrations of IL-4 or KFR (FIG. 13a).

Dendritic Cell Differentiation Assay

IL-4, in combination with GM-CSF, induces the in vitro differentiation of dendritic cells (DCs) from human monocytes. The relative roles of the Type-I or Type-II receptors for this process have yet to be elucidated. Given that super-4 preferentially binds γc and KFR is skewed towards IL-13Rα1 ligation, the requirements for the γc and IL-13Rα1 pathways during human DC differentiation were elucidated.

CD14$^+$ monocytes were isolated (>97% purity) from peripheral blood mononuclear cells obtained from healthy blood donors (Stanford Blood Center) by density centrifugation using a Rosette®Sep Human Monocyte Enrichment Cocktail (Stem Cell Technologies) followed by magnetic separation with anti-CD14 conjugated microbeads (Miltenyi Biotec). 5×10$^5$ CD14$^+$ monocytes were subsequently cultured with 50 ng/mL GM-CSF alone or with the indicated concentrations of IL-4, KFR or super-4 in 12-well plates (Corning) containing IMDM medium (Gibco®) supplemented with 10% human AB serum, 100 U/mL penicillin, 100 μg/mL streptomycin, 2 mM L-glutamine, sodium pyruvate, non-essential amino acids and 50 μM 2-ME. Fresh cytokines were added on days 2 and 4.

Cells were processed on day 6 with 5 mM EDTA and subsequently stained with DAPI (Invitrogen), fluorescently labeled isotype control mAbs, or mAbs against CD14, CD86, CD209 and HLA-DR (BD Biosciences). Dendritic cell differentiation was assessed by flow cytometry with a BD LSRII flow cytometer and Mean fluorescent intensity of cell surface marker expression was detected and analyzed by FlowJo (Treestar).

Figure 23:
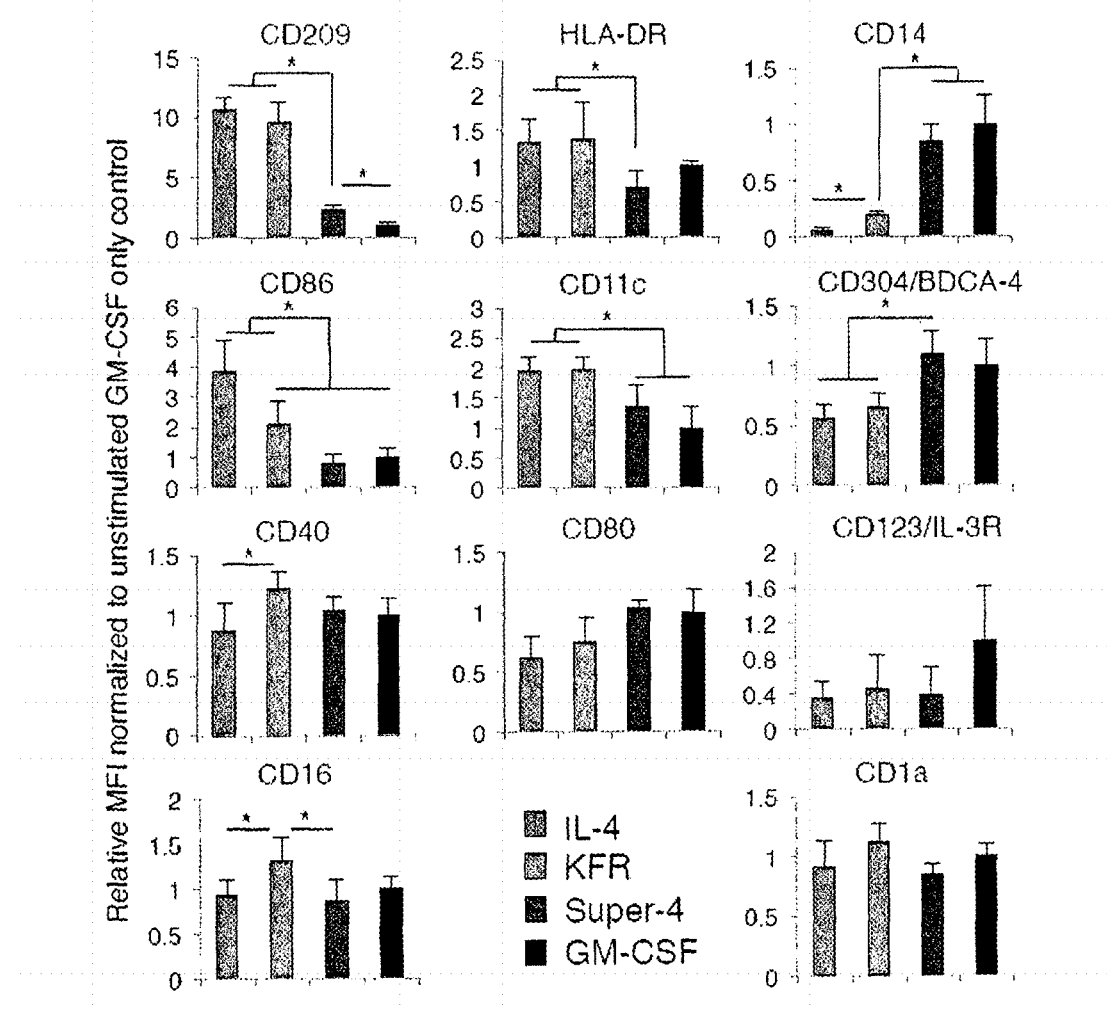
FIG. 23 illustrates differential expression of surface markers in the presence of IL-4, KFR or super-4. Monocytes were cultured for 7 days with 50 ng/ml GM-CSF, with or without IL-4, KFR or super-4 (20 ng/ml). Data represent mean±SD from 3 healthy donors (normalized to GM-CSF alone group). *p<0.05 (paired T-test). CD1c (BDCA-1) and CD141 (BDCA-3) were not detected above background levels.

While IL-4 and KFR elicited monocyte differentiation into DCs as assessed by the upregulation of CD209, CD86 and HLA-DR (FIG. 13b and FIG. 22), super-4 failed to do so suggesting that DC differentiation is mainly driven by signaling through the Type-II IL-4 receptor complex, which is poorly engaged by super-4. The maturation of monocytes into DCs is also associated with down regulation of CD14; super-4 was less effective than KFR or IL-4 in down-regulation CD14. (FIG. 13b). Additionally, analysis of further markers used to distinguish different dendritic cell subsets show that cells induced by GM-CSF with or without super-4 are phenotypically identical (FIG. 23), implying that super-4-induced cells were incompletely differentiated rather than differentiated into a distinct dendritic cell subset.

Figure 14:
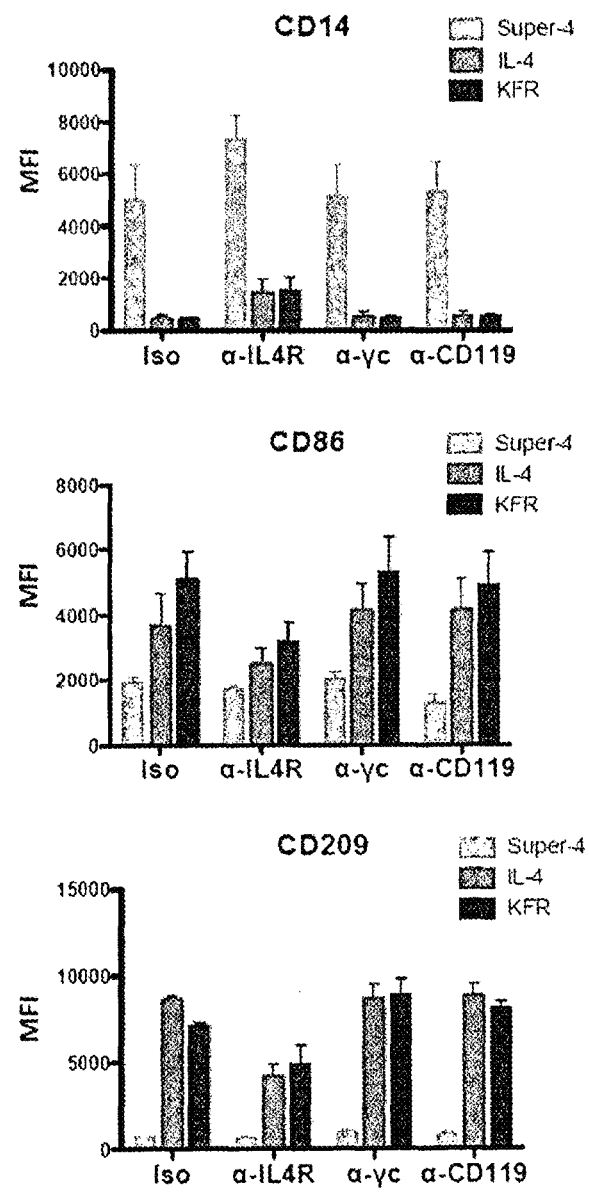
FIG. 14 depicts that superkines delineate that dendritic cell maturation relies on the activation of the type II IL-4 receptor complex. CD14, CD86 and CD209 surface marker expression was used to indicate superkine impact on DC maturation. For this experiment CD14+ monocytes were isolated (>97% purity) and cultured with 50 ng/mL GM-CSF and 2 μg/ml of IL-4, KFR or super-4 in the presence of the indicated antibodies. Cells were processed on day 6 and subsequently stained with DAPI, fluorescently labeled isotype control mAbs, or mAbs against CD14, CD86 and CD209. Data (mean and SEM) are from 3 donors.

To confirm the relative roles of Type-I and Type-II IL-4 receptor complexes in DC differentiation, it was shown herein that anti-IL-4Rα(Type I and Type II receptor specific) diminished the expression of CD86 and CD209 in response to IL-4 and KFR while anti-γc (Type I receptor specific) failed to do so (FIG. 14). As before, super-4 caused very modest induction of these markers. Super-4 induced CD14 down-regulation was partially inhibited by anti-IL-4Rα but not anti-γc. Interestingly when neutralizing antibodies against γc were used, IL-4 and KFR still induced the same level of DC maturation as in the control condition (FIG. 14), confirming that DC differentiation occurs via the type-II IL-4 receptor complex.

Figure 15:
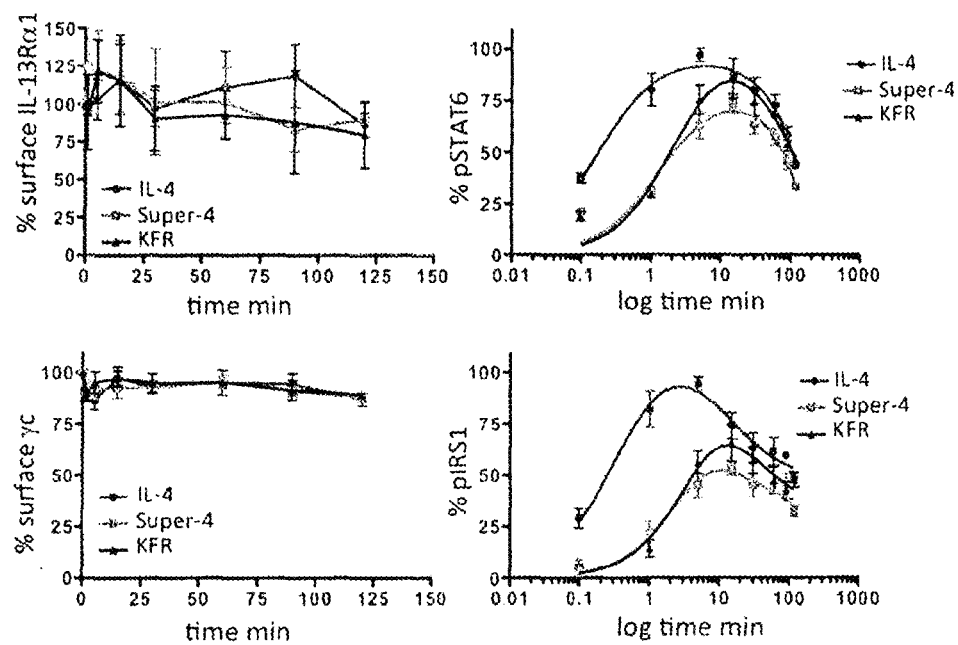
FIG. 15 depicts signaling and internalization kinetics of IL-4 and the two superkines in monocytes. CD14+ monocytes were isolated (>97% purity) from peripheral blood mononuclear cells and stimulated with 30 pM of IL-4, super-4 or KFR for the indicated times. Cells were then harvested and either, kept at 4° C. and stained with antibodies specific for IL-13Rα1 and γc receptor chains for the receptor downregulation experiments or fixed with 4% PFA, permeabilized with 100% methanol and stained with phospho-specific antibodies against STAT6 and IRS1 for the signaling kinetics experiments. In both cases, cells were analyzed by flow cytometry. Data (mean and SEM) are from 4 healthy donors.
Figure 19:
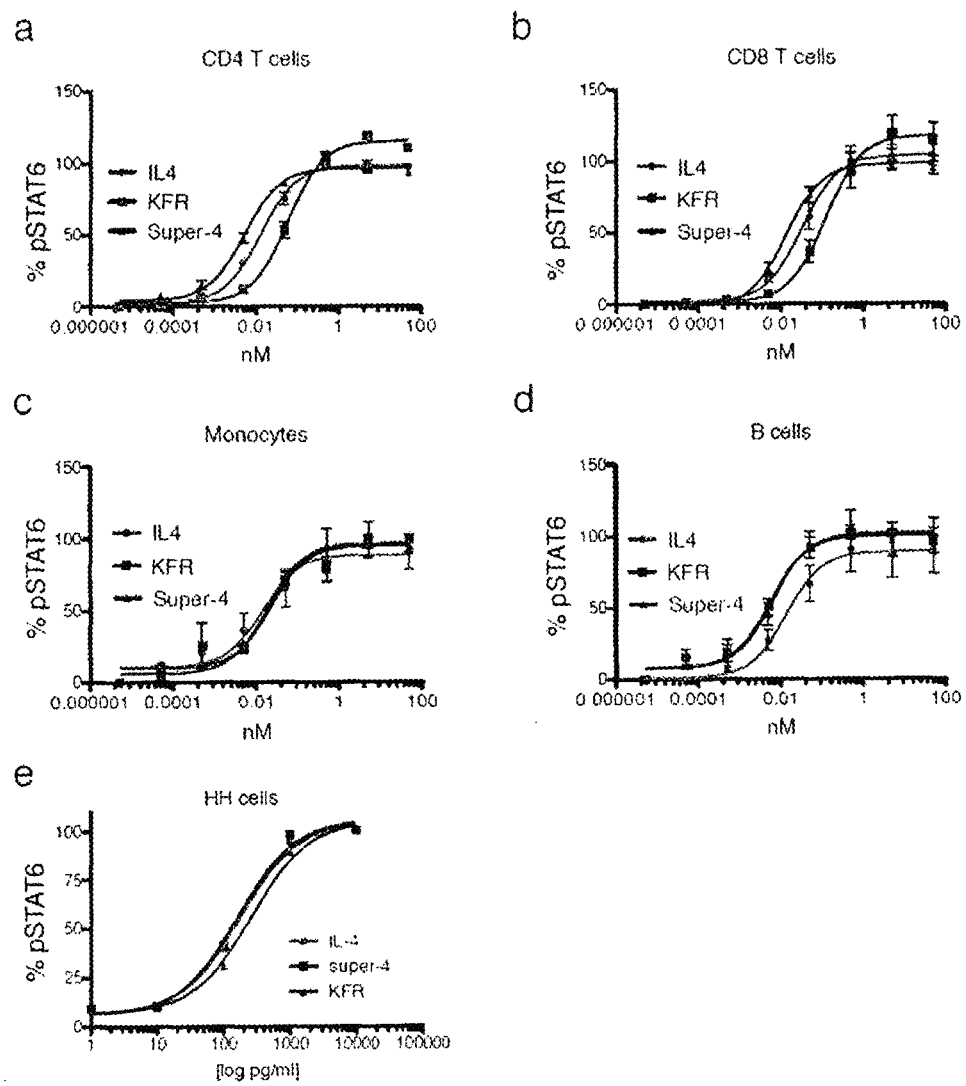
FIG. 19 illustrates STAT6 phosphorylation induced by IL-4 and the two superkines. Cells were stimulated with the indicated doses of IL-4 and the two superkines and the levels of STAT6 phosphorylation were detected in (a) CD4 T cells, (b) CD8 T cells, (c) Monocytes, (d) B cells and (e) HH cells using phospho-STAT6 specific antibodies fluorescently labeled and flow cytometry. Mean and SEM were obtained from three different experiments.

Example 8: Signal Activation Profile Induced by IL-4 and Superkines in Monocytes The ability of super-4 to induce DC differentiation was determined because IL-4 and the two superkines activated STAT6 to the same extent in monocytes (FIG. 11(e), FIG. 12, and FIG. 19). Purified monocytes were treated with two doses of cytokines, one dose corresponding to the P-STAT6 EC50 value (30 pM) (FIG. 15) and another dose corresponding to saturation (50 nM) (FIG. 20). The levels of STAT6 and IRS1 phosphorylation as well as the downregulation of the γc and IL-13Rα1 receptors were analyzed at the indicated times. At low doses, super-4 and KFR exhibited delayed activation of STAT6 and IRS1 when compared to IL-4. No significant internalization of either γc or IL-13Rα1 was observed (FIG. 15). At high doses, the three cytokines induced the same kinetics profile of STAT6 and IRS1 activation. KFR exhibited stronger internalization of IL-13Rα1 at later times of stimulation (FIG. 20). Overall, these results show a lack of correlation between surface receptor internalization and signaling activation. Moreover, the delayed kinetics of signaling activation alone cannot explain the inefficiency of super-4 to induce DC differentiation, suggesting that Type-II receptor specific signaling is required for DC differentiation.

Example 9: Gene Expression Profile Induced by IL-4 and Superkines in Monocytes

To gain qualitative insights into the extent of redundancy of genetic programs induced by IL-4 and superkines in differentiating DCs, genome-wide analysis of gene expression in response to WT IL-4 and the two superkines in monocytes treated simultaneously with GM-CSF was performed. CD14+ monocytes were isolated from 5 healthy donors and stimulated for 6 hours with 50 ng/ml GM-CSF alone, or with 20 ng/ml of IL-4, Super-4 or KFR. Cells were washed in PBS and lyzed in 1 ml TRIzol reagent (Sigma). Total RNA was isolated using a combined TRIzol/RNeasy Micro (Qiagen) protocol. RNA quality was confirmed with a 2100 Bioanalyzer (Agilent). cDNA was generated and labeled using the Two-color Low Input Quick Amp Labeling kit (Agilent), with single treatment samples (GM-CSF alone) labeled with Cy3 and dual treatment samples labeled with Cy5. For each donor, sample from each Cy5-labeled dual treatment (GM-CSF with either IL-4, Super-4 or KFR) was co-hybridized with the corresponding Cy3-labeled single treatment with GM-CSF onto 8×60K SurePrint G3 Gene expression microarrays (Agilent) and processed as per manufacturer's instructions. Raw data were normalized using Feature Extraction software (Agilent). Paired T-test analysis was used for statistical analysis of changes between dual and single treatment, and between variants. Gene expression analysis was performed on GeneSpring GX11.5 and Excel. Entities only detected in less than 6 arrays, quality control probes and probes for long intergenic non-coding RNAs were excluded. Entities for which there was a significant change (paired t-test) in at least one dual treatment group compared to GM-CSF alone (Cy5 vs Cy3) were retained. Fold-change statistical analysis between two given cytokines was determined by paired t-test. Microarray data have been submitted to the Gene Expression Omnibus (GEO) Database at NCBI (GEO series accession number: GSE40200).

Figure 16:
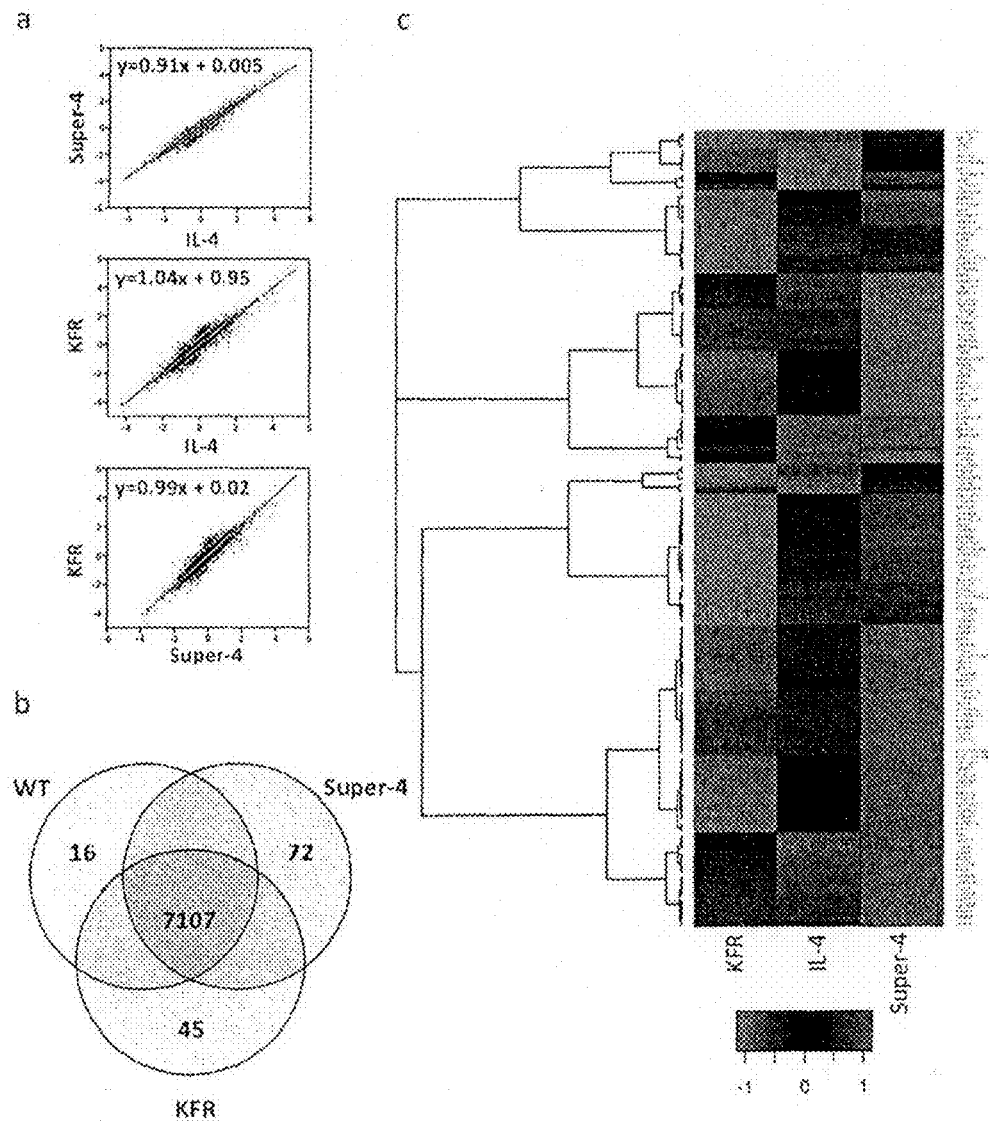
FIG. 16 depicts gene expression profiles induced by IL-4 and the two superkines in monocytes. Highly purified monocytes from 5 healthy donors were stimulated for six hours with GM-CSF alone or combined with IL-4 or the two superkines and their RNA was extracted and analyze by two-color Agilent microarrays (60,000 features). (a) Scatter plot correlation comparing the gene induction by the three cytokines are shown. (b) Venn diagram where genes significantly down/up-regulated by the three cytokines, when compared to the GM-CSF control condition, is shown. (c) Heatmap showing a selected list of genes (Table 4) significantly regulated by IL-4/super-4 vs KFR, IL-4/KFR vs super-4 or IL-4 vs super-4/KFR (p<0.05, paired T-test). Blue color denotes higher expression and red color denotes lower expression.

As shown by scatter plot correlation, the three cytokines induce the vast majority of genes to the same extent (FIG. 16a). However, interestingly, minor pockets of gene expression specificity can also be observed between IL-4 and the two superkines. A considerable number of genes were significantly induced by only one or two of the cytokines used, as shown by the Venn diagram in FIG. 16b. The heatmap in FIG. 16c shows a representative set of cytokine-selective genes where clear differences in the expression patterns induced by IL-4 and the two superkines were observed. A list of genes regulated differentially by superkines and IL-4 in monocytes is presented in Table 4. DC-specific genes such as TPAI, HLA-DPA and CISH were clearly induced to a higher level by IL-4 and KFR than by super-4, consistent with specific signals coming from the Type-II IL-4 receptor that could bias the dendritic cell differentiation process induced by IL-4.

TABLE 4

Fold induction (mean, first three columns of data) and p values (paired t-test, last three columns of data) of superkine-selective genes.

| Gene ID | IL-4 mean | Super-4 mean | KFR mean | PPT (W-S) | PTT (W-K) | PPT (S-K) |
|---|---|---|---|---|---|---|
| GPR183 | 1.361 | 1.544 | 1.225 | 0.069 | 0.009 | 0.003 |
| ASB1 | −0.639 | −0.832 | −0.585 | 0.235 | 0.001 | 0.007 |
| SLA | 4.143 | 4.329 | 4.023 | 0.236 | 0.030 | 0.040 |
| BIRC2 | −0.312 | −0.258 | −0.351 | 0.280 | 0.024 | 0.010 |
| TMEM216 | −0.302 | −0.423 | −0.257 | 0.307 | 0.006 | 0.003 |
| NMD3 | 0.795 | 0.984 | 0.742 | 0.399 | 0.019 | 0.039 |
| FUNDC2 | 0.162 | 0.232 | 0.126 | 0.473 | 0.012 | 0.037 |
| GLTID1 | −0.848 | −1.013 | −0.856 | 0.910 | 0.029 | 0.024 |
| ANKRD23 | −0.024 | −0.693 | −0.264 | 0.176 | 0.037 | 0.016 |
| SP110 | −0.386 | −0.821 | −0.520 | 0.282 | 0.036 | 0.047 |
| LIX1L | −0.103 | −0.395 | −0.171 | 0.669 | 0.049 | 0.018 |
| POMZP3 | −0.078 | 0.223 | −0.067 | 0.939 | 0.011 | 0.014 |
| POLDIP3 | 0.051 | 0.227 | 0.143 | 0.138 | 0.032 | 0.003 |
| CNST | −0.359 | −0.932 | −0.670 | 0.233 | 0.005 | 0.042 |
| FBLN5 | 1.714 | 2.249 | 1.846 | 0.503 | 0.017 | 0.017 |
| UTRN | 1.096 | 1.223 | 0.955 | 0.279 | 0.035 | 0.039 |
| GPR68 | −2.802 | −2.817 | −2.479 | 0.001 | 0.000 | 0.597 |
| EMP1 | −2.299 | −2.310 | −1.986 | 0.001 | 0.001 | 0.790 |
| C13orf31 | −1.467 | −1.414 | −1.166 | 0.001 | 0.004 | 0.442 |
| ALDH2 | 0.944 | 0.948 | 0.728 | 0.002 | 0.031 | 0.963 |
| BRD7 | −0.480 | −0.438 | −0.339 | 0.003 | 0.035 | 0.068 |
| CUTC | 0.631 | 0.714 | 0.564 | 0.003 | 0.040 | 0.201 |
| TOR3A | 1.440 | 1.484 | 1.218 | 0.004 | 0.022 | 0.408 |
| APBB1IP | 1.782 | 1.845 | 1.609 | 0.004 | 0.008 | 0.331 |
| CCL2 | −4.117 | −4.266 | −3.431 | 0.005 | 0.007 | 0.419 |
| KANK1 | −2.617 | −2.467 | −2.059 | 0.006 | 0.043 | 0.376 |
| DPYSL2 | 1.093 | 1.111 | 0.936 | 0.006 | 0.018 | 0.643 |
| APOL6 | 1.646 | 1.808 | 1.386 | 0.006 | 0.006 | 0.085 |
| BCL6 | −1.346 | −1.322 | −1.179 | 0.006 | 0.012 | 0.445 |

TABLE 4-continued

Fold induction (mean, first three columns of data) and p values (paired t-test, last three columns of data) of superkine-selective genes.

| Gene ID | IL-4 mean | Super-4 mean | KFR mean | PPT (W-S) | PTT (W-K) | PPT (S-K) |
|---|---|---|---|---|---|---|
| RPL18A | 0.600 | 0.535 | 0.387 | 0.009 | 0.023 | 0.285 |
| NDUFV1 | 0.706 | 0.701 | 0.534 | 0.010 | 0.002 | 0.868 |
| HLA-DPA1 | 0.518 | 0.419 | 0.293 | 0.010 | 0.049 | 0.133 |
| HEBP1 | −1.656 | −1.581 | −1.383 | 0.011 | 0.030 | 0.485 |
| FRY | −1.784 | −1.592 | −1.416 | 0.011 | 0.020 | 0.115 |
| C13orf18 | −1.647 | −1.580 | −1.243 | 0.013 | 0.038 | 0.571 |
| CAT | 1.444 | 1.387 | 1.212 | 0.014 | 0.001 | 0.313 |
| BAI1 | −1.312 | −1.242 | −1.024 | 0.014 | 0.018 | 0.272 |
| MED30 | −1.048 | −0.919 | −0.727 | 0.014 | 0.036 | 0.244 |
| TLR1 | −1.409 | −1.392 | −1.170 | 0.015 | 0.013 | 0.681 |
| TRIB3 | −2.562 | −2.576 | −2.318 | 0.016 | 0.001 | 0.857 |
| PTGS2 | −4.304 | −4.276 | −3.757 | 0.017 | 0.030 | 0.843 |
| RGS1 | −3.528 | −3.737 | −3.027 | 0.017 | 0.011 | 0.414 |
| MR1 | 0.501 | 0.544 | 0.397 | 0.018 | 0.001 | 0.368 |
| HOMER3 | −1.025 | −1.016 | −0.877 | 0.019 | 0.032 | 0.772 |
| TCHH | −2.325 | −2.623 | −1.958 | 0.019 | 0.034 | 0.328 |
| PEX13 | −0.876 | −0.766 | −0.635 | 0.019 | 0.013 | 0.186 |
| PLSCR1 | −1.664 | −1.499 | −1.253 | 0.019 | 0.022 | 0.153 |
| FAU | 0.315 | 0.273 | 0.197 | 0.019 | 0.041 | 0.321 |
| AK3L1 | −1.313 | −1.439 | −1.089 | 0.020 | 0.037 | 0.460 |
| NUMB | −1.239 | −1.225 | −1.041 | 0.020 | 0.013 | 0.823 |
| CXCL1 | −3.749 | −3.567 | −2.932 | 0.021 | 0.019 | 0.594 |
| SAV1 | −1.783 | −1.872 | −1.584 | 0.023 | 0.047 | 0.539 |
| TrEMBL | −0.715 | −0.632 | −0.445 | 0.025 | 0.039 | 0.245 |
| ZAK | −0.791 | −0.898 | −0.628 | 0.027 | 0.037 | 0.347 |
| TCEB2 | 0.430 | 0.427 | 0.328 | 0.028 | 0.038 | 0.930 |
| CXCL3 | −3.772 | −3.851 | −3.136 | 0.028 | 0.009 | 0.688 |
| MTF1 | −1.430 | −1.282 | −1.073 | 0.029 | 0.048 | 0.133 |
| MECP2 | −0.804 | −0.700 | −0.574 | 0.032 | 0.012 | 0.099 |
| GMFG | −0.722 | −0.676 | −0.607 | 0.033 | 0.039 | 0.459 |
| LRRC25 | −1.256 | −1.309 | −0.992 | 0.034 | 0.031 | 0.731 |
| MLH1 | −0.950 | −0.888 | −0.737 | 0.035 | 0.032 | 0.364 |
| PSMA1 | −0.315 | −0.265 | −0.212 | 0.035 | 0.037 | 0.242 |
| PAM | −0.947 | −1.033 | −0.677 | 0.035 | 0.004 | 0.312 |
| LOC283050 | −1.567 | −1.523 | −1.351 | 0.036 | 0.009 | 0.644 |
| LOC100292409 | −0.740 | −0.703 | −0.306 | 0.039 | 0.026 | 0.855 |
| C2CD2 | 1.050 | 1.058 | 0.750 | 0.039 | 0.006 | 0.899 |
| TAP1 | 0.516 | 0.483 | 0.389 | 0.041 | 0.030 | 0.515 |
| ADAM10 | −1.495 | −1.481 | −1.229 | 0.041 | 0.035 | 0.928 |
| SNCA | −1.466 | −1.362 | −1.148 | 0.041 | 0.014 | 0.513 |
| CKAP4 | −2.725 | −2.800 | −2.324 | 0.042 | 0.003 | 0.597 |
| DOK3 | −1.694 | −1.692 | −1.462 | 0.042 | 0.006 | 0.984 |
| CISH | 1.088 | 1.030 | 0.887 | 0.042 | 0.020 | 0.438 |
| ARMC8 | −1.117 | −1.089 | −0.769 | 0.043 | 0.048 | 0.882 |
| BEST1 | −1.281 | −1.268 | −1.082 | 0.044 | 0.036 | 0.807 |
| CARD6 | −1.550 | −1.474 | −1.204 | 0.045 | 0.001 | 0.505 |
| ZNF366 | 3.182 | 3.166 | 2.895 | 0.046 | 0.035 | 0.885 |
| SORT1 | 1.074 | 1.098 | 0.913 | 0.046 | 0.011 | 0.737 |
| RNF149 | −1.619 | −1.631 | −1.333 | 0.047 | 0.004 | 0.878 |
| KCNE1L | −1.687 | −1.353 | −1.110 | 0.048 | 0.032 | 0.175 |
| C21orf7 | −3.142 | −2.878 | −2.454 | 0.049 | 0.040 | 0.084 |
| TBL1XR1 | 0.759 | 0.813 | 0.575 | 0.049 | 0.043 | 0.204 |
| AMOTL1 | 0.261 | −0.026 | −0.758 | 0.015 | 0.029 | 0.208 |
| ADCY4 | −0.017 | −0.066 | 0.137 | 0.017 | 0.009 | 0.498 |
| LOC100128348 | 0.166 | 0.295 | 0.522 | 0.033 | 0.002 | 0.307 |
| PRB3 | 0.276 | 0.275 | −0.480 | 0.044 | 0.013 | 0.998 |
| TRIM59 | −0.293 | −0.329 | −0.660 | 0.045 | 0.017 | 0.776 |
| TSR2 | −0.129 | −0.204 | −0.302 | 0.008 | 0.002 | 0.122 |
| FARS2 | 0.868 | 0.573 | 0.585 | 0.001 | 0.804 | 0.004 |
| MEI1 | −1.908 | −1.762 | −1.715 | 0.003 | 0.392 | 0.050 |
| AK1 | 0.852 | 0.674 | 0.627 | 0.008 | 0.149 | 0.008 |
| ZNF512B | 1.508 | 1.282 | 1.289 | 0.011 | 0.897 | 0.013 |
| SPSB1 | 1.433 | 1.065 | 1.169 | 0.011 | 0.368 | 0.015 |
| ATP6V0C | −0.269 | −0.195 | −0.178 | 0.013 | 0.653 | 0.013 |
| ZFYVE16 | −1.122 | −0.958 | −0.904 | 0.015 | 0.455 | 0.013 |
| RP11-94I2.2 | −0.732 | −0.541 | −0.522 | 0.015 | 0.851 | 0.033 |
| P4HA1 | −0.527 | −0.374 | −0.372 | 0.008 | 0.971 | 0.043 |
| CAB39 | −1.100 | −0.911 | −0.820 | 0.023 | 0.384 | 0.007 |
| KCTD11 | −0.434 | −0.597 | −0.554 | 0.023 | 0.620 | 0.042 |
| BTN3A2 | 0.751 | 0.578 | 0.571 | 0.025 | 0.868 | 0.047 |
| C1orf56 | −1.137 | −0.974 | −0.910 | 0.027 | 0.261 | 0.009 |
| SPIRE1 | −0.933 | −0.740 | −0.653 | 0.028 | 0.380 | 0.007 |
| PRDM8 | −2.687 | −2.278 | −2.293 | 0.028 | 0.941 | 0.024 |
| ZNF655 | −0.429 | −0.294 | −0.251 | 0.030 | 0.391 | 0.047 |

TABLE 4-continued

Fold induction (mean, first three columns of data) and p values (paired t-test, last three columns of data) of superkine-selective genes.

| Gene ID | IL-4 mean | Super-4 mean | KFR mean | PPT (W-S) | PTT (W-K) | PPT (S-K) |
|---|---|---|---|---|---|---|
| TCEB3 | 0.356 | 0.515 | 0.499 | 0.031 | 0.806 | 0.031 |
| SAMM50 | 0.599 | 0.479 | 0.471 | 0.032 | 0.780 | 0.048 |
| COX7A2 | −0.644 | −0.538 | −0.482 | 0.035 | 0.400 | 0.040 |
| ABCF3 | 0.769 | 0.645 | 0.616 | 0.036 | 0.587 | 0.041 |
| ATP5G2 | 0.597 | 0.489 | 0.460 | 0.036 | 0.396 | 0.037 |
| H2A.2 | 0.270 | 0.385 | 0.382 | 0.037 | 0.910 | 0.017 |
| AP1S2 | −2.491 | −1.801 | −1.582 | 0.042 | 0.441 | 0.002 |
| YIPF5 | −0.546 | −0.756 | −0.610 | 0.046 | 0.102 | 0.034 |
| IGBP1 | 0.514 | 0.430 | 0.376 | 0.046 | 0.237 | 0.006 |
| DAZAP1 | −0.546 | −0.335 | −0.249 | 0.049 | 0.356 | 0.032 |
| PSD4 | 0.702 | 0.468 | 0.232 | 0.010 | 0.015 | 0.010 |
| PSPN | −0.754 | 0.225 | −0.027 | 0.016 | 0.040 | 0.003 |
| STX10 | 0.622 | 0.089 | 0.136 | 0.004 | 0.731 | 0.009 |
| CNP | 0.206 | 0.048 | 0.064 | 0.008 | 0.739 | 0.029 |
| TAFI63 | −1.184 | −0.209 | 0.032 | 0.009 | 0.217 | 0.012 |
| ASB6 | 0.321 | 0.233 | 0.096 | 0.010 | 0.061 | 0.030 |
| LY6E | 1.431 | 1.167 | 1.180 | 0.018 | 0.490 | 0.008 |
| LRRC37A3 | 0.345 | 0.066 | 0.048 | 0.024 | 0.829 | 0.007 |
| ADPRH | −0.309 | −0.194 | −0.059 | 0.027 | 0.187 | 0.019 |
| GPR150 | −0.532 | −0.437 | −0.326 | 0.027 | 0.124 | 0.042 |
| CCPG1 | −0.633 | −0.201 | −0.197 | 0.028 | 0.963 | 0.014 |
| PDLIM5 | −0.345 | −0.099 | −0.181 | 0.032 | 0.352 | 0.029 |
| REPIN1 | 0.864 | 0.662 | 0.603 | 0.039 | 0.407 | 0.042 |
| MKRN1 | −0.164 | −0.103 | 0.019 | 0.040 | 0.145 | 0.011 |
| PRDM13 | −0.555 | 0.042 | 0.004 | 0.041 | 0.694 | 0.017 |
| TBCA | −0.459 | −0.282 | −0.238 | 0.042 | 0.573 | 0.009 |
| COPS7B | 1.131 | 0.512 | 0.199 | 0.049 | 0.407 | 0.002 |
| NOTCH2NL | −0.906 | −0.480 | −0.386 | 0.009 | 0.245 | 0.038 |
| CD44 | −0.580 | −0.417 | −0.377 | 0.018 | 0.436 | 0.006 |
| GSTK1 | 0.545 | 0.407 | 0.207 | 0.044 | 0.129 | 0.002 |
| SLC41A3 | −0.430 | −0.255 | −0.220 | 0.007 | 0.540 | 0.003 |

Example 10: Cytokine Secretion Profile Induced by IL-4 and the Two Superkines

To further assess the functionality of the DCs induced by the engineered cytokines, the secretion patterns of cytokines, chemokines and growth factors were compared by performing a Luminex assay on supernatant of cells cultured for 8 days with or without LPS stimulation during the last 24 hours.

For Luminex cytokine profiling, culture supernatant was collected on day 8 (with or without 24 h stimulation with 2 μg/ml LPS). Human 51-plex kits were purchased from Affymetrix and used according to the manufacturer's recommendations with modifications as described below. Briefly, samples were mixed with antibody-linked polystyrene beads on 96-well filter-bottom plates and incubated at room temperature for 2 h followed by overnight incubation at 4° C. Plates were vacuum-filtered and washed twice with wash buffer, then incubated with biotinylated detection antibody for 2 h at room temperature. Samples were then filtered and washed twice as above and resuspended in streptavidin-PE. After incubation for 40 minutes at room temperature, two additional vacuum washes were performed, and the samples resuspended in Reading Buffer. Plates were read using a Luminex 200 instrument with a lower bound of 100 beads per sample per cytokine. MFIs were normalized to values from unstimulated cells cultured with GM-CSF only.

Figure 17:
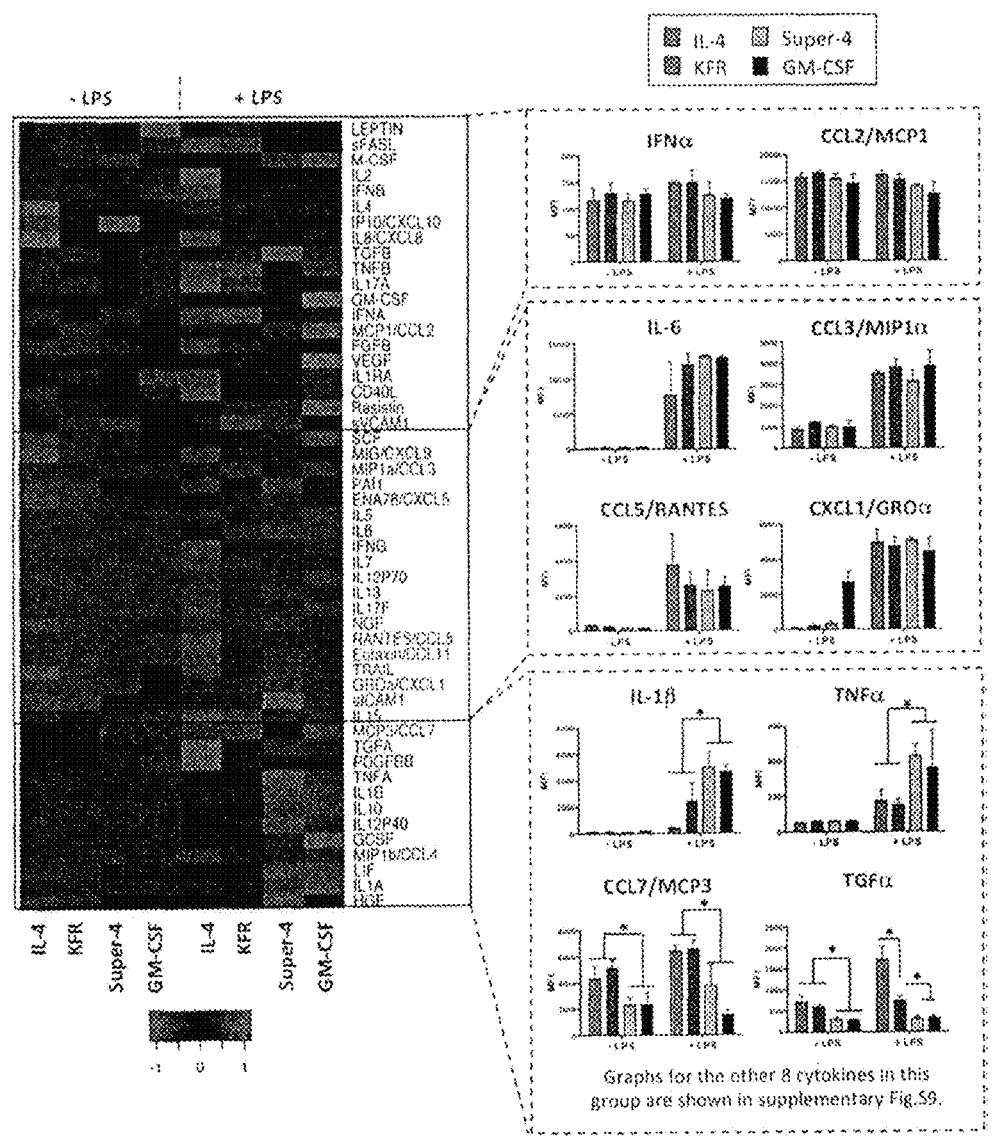
FIG. 17 depicts distinct patterns of cytokine secretion induced by IL-4 and the two superkines in immature and LPS-matured DCs. Purified monocytes from 3 healthy donors were cultured for 7 days with GM-CSF (50 ng/ml) alone or combined with IL-4, KFR or super-4 (20 ng/ml), then stimulated (or not) with LPS (2 μg/ml) for another 24 hours. Culture supernatant was assessed by Luminex for relative amounts of 51 cytokines, chemokines and growth factors (listed by the heatmap). The panels on the right of the heatmap are representative examples of products whose secretion was either unchanged (n=19), increased by LPS stimulation only (n=20), or modulated by superkines in the presence or absence of LPS (n=12). Data represent mean and SD from 3 healthy donors (normalized to GM-CSF alone group). Paired T-test was used to determine significant changes, *p<0.05).
Figure 21:
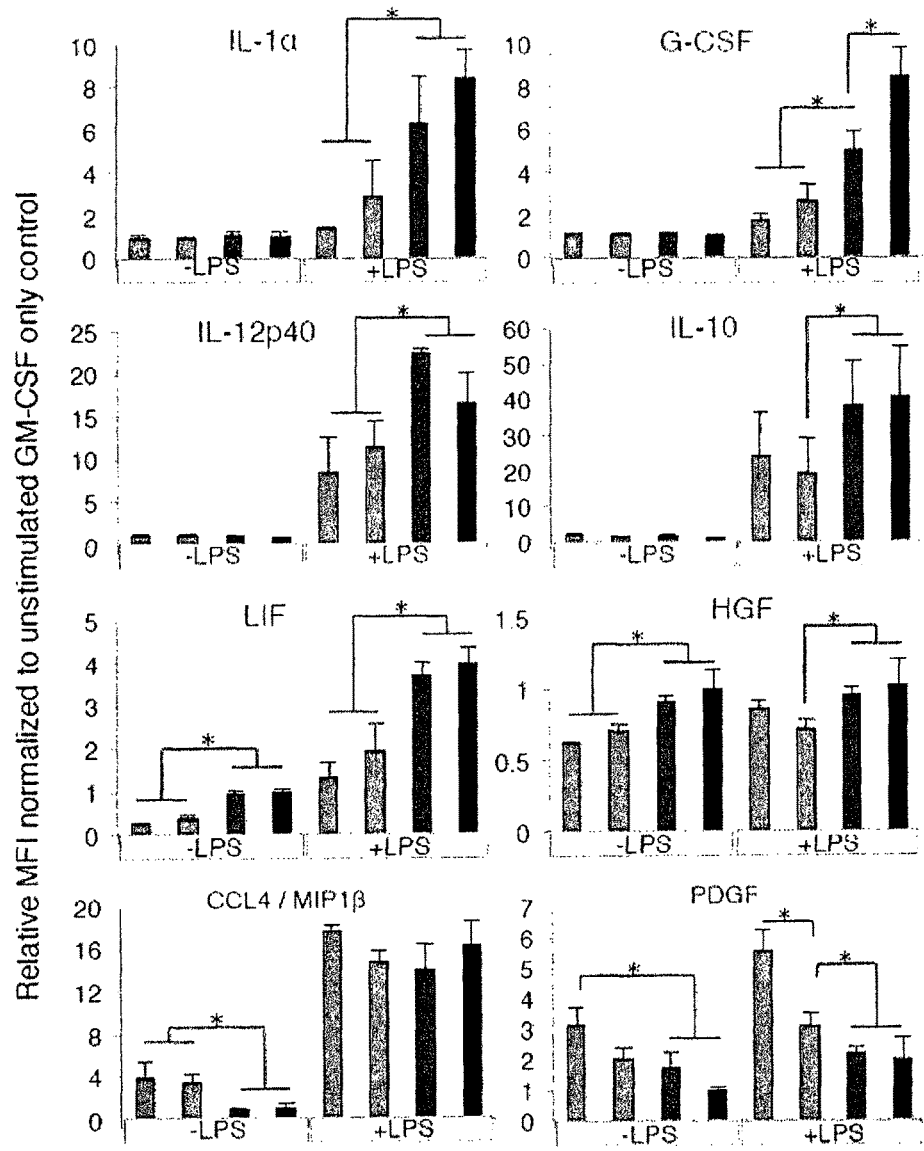
FIG. 21 illustrates differential induction of cytokine secretion by IL-4, KRF and super-4. Monocytes were cultured for 7 days with 50 ng/ml GM-CSF, with or without IL-4, KFR or super-4 (20 ng/ml) then stimulated for 24 h with LPS (2 mg/ml), data represent mean±SD from 3 healthy donors (normalized to unstimulated GM-CSF alone group). *p<0.05 (paired T-test).

Among the 51 analytes, 20 showed no difference in expression between treatments (superkines and LPS) and 19 were upregulated by LPS (most notably IL-6, CCL3, CCL5, and CXCL1) without difference between IL-4 and the superkines (FIG. 17). The expression of the remaining 12 products discriminated the cells induced by GM-CSF only or GM-CSF+super-4 from the DCs induced by GM-CSF+IL-4 or KFR (FIG. 17 and FIG. 21). The former two subsets were very similar and produced more G-CSF, HGF, IL-1α, IL-1β, IL-10, IL-12p40, LIF, TNFα, and less MCP3, MIP1β, PDGF, TGFα than the latter two, also very similar, subsets. Most of the differences were seen after LPS stimulation but some also existed in non-activated cells. Altogether, these data demonstrate that super-4 had no effect over that of GM-CSF alone on monocytes, while the addition of IL-4 or KFR led to phenotypically and functionally different DCs. Thus, the engineered cytokines appear to possess new and distinct functional activities.

We claim:

1. A composition comprising an IL-4 mutein, wherein the IL-4 mutein results in higher affinity binding to a shared cytokine receptor relative to a wild-type cytokine, and wherein the IL-4 mutein comprises one or two amino acid substitutions at positions S128 and/or S129, wherein the amino acid numbering is in accordance with wild-type human IL-4 of SEQ ID NO: 4.

2. The composition of claim 1, wherein the IL-4 mutein results in higher affinity binding to a first shared cytokine receptor relative to a wild-type cytokine and reduced affinity to a second shared cytokine receptor relative to a wild-type cytokine.

3. The composition of claim 2, wherein the first shared cytokine receptor is expressed at lower levels than the second shared cytokine receptor.

4. The composition of claim 2, wherein the first shared cytokine receptor is expressed at higher levels than the second shared cytokine receptor.

5. The composition of claim 2, wherein the reduction in affinity is at least 5-fold.

6. The composition of claim 2, wherein the first shared cytokine receptor is γc and the second shared cytokine receptor is IL-13Rα1.

7. The composition of claim 2, wherein the first shared cytokine receptor is IL-13Rα1 and the second shared cytokine receptor is γc.

8. The composition of claim 2, wherein the first and second shared cytokine receptors are γc and IL-13Rα1.

9. The composition of claim 1, wherein the IL-4 mutein results in higher affinity binding to a first and a second shared cytokine receptor relative to a wild-type cytokine.

10. The composition of claim 1, wherein the increase in affinity is at least 10-fold.

11. The composition of claim 1, wherein the shared cytokine receptor is common γ chain (γc) or interleukin-13 receptor alpha 1 (IL-13Rα1).

12. The composition of claim 1, wherein the IL-4 mutein further comprises one or more amino acid substitutions at positions selected from the group consisting of: K117, T118, R121, E122, Y124, and S125 wherein the amino acid numbering is in accordance with wild-type human IL-4 of SEQ ID NO: 4.

13. The composition of claim 12, wherein the IL-4 mutein comprises one or more amino acid substitutions selected from the group consisting of: K117R, T118V, R121Q, E122S, Y124W, S125F, S128G, and S129A, wherein the amino acid numbering is in accordance with wild-type human IL-4 of SEQ ID NO: 4.

14. The composition of claim 12, wherein the IL-4 mutein comprises the following amino acid substitutions: K117R, T118V, R121Q, E122S, Y124W, S125F, S128G, and S129A, wherein the amino acid numbering is in accordance with wild-type human IL-4 of SEQ ID NO: 4.

* * * * *